US008816029B2

(12) United States Patent
Wang et al.

(10) Patent No.: US 8,816,029 B2
(45) Date of Patent: *Aug. 26, 2014

(54) COMPOSITIONS AND ARTICLES COMPRISING POLYMERIZABLE IONIC LIQUID MIXTURE, AND METHODS OF CURING

(75) Inventors: Yizhong Wang, Woodbury, MN (US); Joel D. Oxman, Minneapolis, MN (US); Larry R. Krepski, White Bear Lake, MN (US); Peiwang Zhu, Woodbury, MN (US); Kevin M. Lewandowski, Inver Grover Heights, MN (US); Brian N. Holmes, St. Paul, MN (US); Richard L. Severance, Stillwater, MN (US); Joseph D. Rule, Cottage Grove, MN (US); Thomas P. Klun, Lakeland, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 139 days.

This patent is subject to a terminal disclaimer.

(21) Appl. No.: 13/380,267

(22) PCT Filed: Aug. 26, 2010

(86) PCT No.: PCT/US2010/046720
§ 371 (c)(1),
(2), (4) Date: Dec. 22, 2011

(87) PCT Pub. No.: WO2011/025847
PCT Pub. Date: Mar. 3, 2011

(65) Prior Publication Data
US 2012/0101184 A1      Apr. 26, 2012

Related U.S. Application Data

(60) Provisional application No. 61/237,992, filed on Aug. 28, 2009, provisional application No. 61/289,169, filed on Dec. 22, 2009, provisional application No. 61/360,185, filed on Jun. 30, 2010.

(51) Int. Cl.
*C08F 26/00* (2006.01)
*C08F 12/30* (2006.01)
*C08F 118/02* (2006.01)
*A61K 6/00* (2006.01)

(52) U.S. Cl.
USPC ........... 526/263; 526/287; 526/312; 526/319; 523/118; 522/167; 522/173

(58) Field of Classification Search
USPC .................. 526/263, 287, 312, 319; 523/118; 522/167, 173
See application file for complete search history.

(56) References Cited

U.S. PATENT DOCUMENTS

| | | |
|---|---|---|
| 3,250,808 A | 5/1966 | Moore, Jr. |
| 3,780,092 A | 12/1973 | Samour |
| 4,049,705 A | 9/1977 | Schwing |
| 4,262,072 A | 4/1981 | Wendling |
| 4,503,169 A | 3/1985 | Randklev |
| 4,619,979 A | 10/1986 | Kotnour |
| 4,843,134 A | 6/1989 | Kotnour |
| 4,872,936 A | 10/1989 | Engelbrecht |
| 4,933,405 A | 6/1990 | Evani |
| 5,063,257 A | 11/1991 | Akahane |
| 5,130,347 A | 7/1992 | Mitra |
| 5,154,762 A | 10/1992 | Mitra |
| 5,159,035 A | 10/1992 | Evani |
| 5,161,041 A | 11/1992 | Abileah |
| 5,175,030 A | 12/1992 | Lu |
| 5,183,597 A | 2/1993 | Lu |
| 5,227,413 A | 7/1993 | Mitra |
| 5,367,002 A | 11/1994 | Huang |
| 5,427,835 A | 6/1995 | Morrison |
| 5,501,707 A | 3/1996 | Schieferstein |
| 5,501,727 A | 3/1996 | Wang |
| 5,520,725 A | 5/1996 | Kato |
| 5,534,322 A | 7/1996 | Ueyama |
| 5,545,676 A | 8/1996 | Palazzotto |
| 5,626,654 A | 5/1997 | Breton |
| 5,637,646 A | 6/1997 | Ellis |

(Continued)

FOREIGN PATENT DOCUMENTS

| | | |
|---|---|---|
| DE | 2750030 | 5/1979 |
| EP | 0537774 | 4/1993 |

(Continued)

OTHER PUBLICATIONS

Abedin et al., "Ionic Liquids: The Link to High-Temperature Molten Salts?", Accounts of Chemical Research, 2007, 40, 1106-1113.
Akimoto et al., "Polymere Modellmembranen", Angew. Chemie., vol. 93, No. 1, 1981, pp. 108-109.
Anderson et al., "Solubility of $CO_2$, $CH_4$, $C_2H_6$, $C_2H_4$, $0_2$, and $N_2$ in 1-Hexyl-3methylpyridinium Bis(trifluoromethylsulfonyl)imide: Comparison to Other Ionic Liquids", Accounts of Chemical Research, 2007, 40, 1208-1216.
Angell et al., "Parallel Developments in Aprotic and Protic Ionic Liquids: Physical Chemistry and Applications", Accounts of Chemical Research, 2007, 40, 1228-1236.

(Continued)

*Primary Examiner* — Michael M Bernshteyn
(74) *Attorney, Agent, or Firm* — 3M Innovative Properties Company; Carolyn A. Fischer

(57) ABSTRACT

Presently described are curable compositions comprising a mixture of at least one (e.g. free-radically) polymerizable ionic liquid and at least one other ethylenically unsaturated monomer, oligomer, or polymer. The polymerizable ionic liquid is characterized as having an air to nitrogen curing exotherm ratio of at least 0.70. Also described are articles and methods of making articles from such curable compositions. A monofunctional polymerizable ionic liquid is also described comprising a non-polymerizable substituted imidazolium cationic group and a polymerizable sulfonate anion.

19 Claims, No Drawings

(56) References Cited

U.S. PATENT DOCUMENTS

| | | | |
|---|---|---|---|
| 5,771,328 A | 6/1998 | Wortman | |
| 5,783,120 A | 7/1998 | Ouderkirk | |
| 5,788,749 A | 8/1998 | Breton | |
| 5,804,610 A | 9/1998 | Hamer | |
| 5,825,543 A | 10/1998 | Ouderkirk | |
| 5,828,488 A | 10/1998 | Ouderkirk | |
| 5,859,089 A | 1/1999 | Qian | |
| 5,871,360 A | 2/1999 | Kato | |
| 5,882,774 A | 3/1999 | Jonza | |
| 5,919,551 A | 7/1999 | Cobb, Jr. | |
| 5,925,715 A | 7/1999 | Mitra | |
| 5,962,550 A | 10/1999 | Akahane | |
| 5,965,632 A | 10/1999 | Orlowski | |
| 6,030,606 A | 2/2000 | Holmes | |
| 6,096,925 A | 8/2000 | Lee | |
| 6,111,696 A | 8/2000 | Allen | |
| 6,277,471 B1 | 8/2001 | Tang | |
| 6,280,063 B1 | 8/2001 | Fong | |
| 6,354,709 B1 | 3/2002 | Campbell | |
| 6,372,829 B1 | 4/2002 | Lamanna | |
| 6,387,981 B1 | 5/2002 | Zhang | |
| 6,428,862 B1 | 8/2002 | Noguchi | |
| 6,572,693 B1 | 6/2003 | Wu | |
| 6,577,358 B1 | 6/2003 | Arakawa | |
| 6,670,436 B2 | 12/2003 | Burgath | |
| 6,730,156 B1 | 5/2004 | Windisch | |
| 6,740,413 B2 | 5/2004 | Klun | |
| 6,750,352 B2 * | 6/2004 | Ono et al. | 548/341.5 |
| 6,759,113 B1 | 7/2004 | Tang | |
| 6,765,038 B2 | 7/2004 | Mitra | |
| 7,074,463 B2 | 7/2006 | Jones | |
| 7,090,721 B2 | 8/2006 | Craig | |
| 7,090,722 B2 | 8/2006 | Budd | |
| 7,156,911 B2 | 1/2007 | Kangas | |
| 7,241,437 B2 | 7/2007 | Davidson | |
| 7,269,327 B2 | 9/2007 | Tang | |
| 7,269,328 B2 | 9/2007 | Tang | |
| 7,345,137 B2 | 3/2008 | Hebrink | |
| 7,452,924 B2 | 11/2008 | Aasen | |
| 7,553,881 B2 | 6/2009 | Salz | |
| 7,649,029 B2 | 1/2010 | Kolb | |
| 7,674,850 B2 | 3/2010 | Karim | |
| 2002/0057564 A1 | 5/2002 | Campbell | |
| 2002/0137825 A1 | 9/2002 | Lamanna | |
| 2003/0129421 A1 | 7/2003 | Terauchi | |
| 2004/0054041 A1 | 3/2004 | Schmidt | |
| 2004/0077775 A1 | 4/2004 | Audenaert | |
| 2006/0216500 A1 | 9/2006 | Klun | |
| 2007/0194275 A1 | 8/2007 | Masuda | |
| 2008/0027231 A1 | 1/2008 | Armstrong | |
| 2008/0051605 A1 | 2/2008 | Ricks-Laskoski | |
| 2008/0070966 A1 | 3/2008 | Elder | |
| 2008/0124555 A1 | 5/2008 | Klun | |
| 2008/0125559 A1 | 5/2008 | Radosz | |
| 2008/0134895 A1 | 6/2008 | Ruud | |
| 2008/0182917 A1 | 7/2008 | Miyabayashi | |
| 2008/0224089 A1 | 9/2008 | Pei | |
| 2009/0017256 A1 | 1/2009 | Hunt | |
| 2009/0060859 A1 | 3/2009 | Garcia Castro | |
| 2009/0142562 A1 | 6/2009 | Miyagawa | |
| 2009/0239969 A1 | 9/2009 | Orlowski | |
| 2011/0021691 A1 | 1/2011 | Chiang | |
| 2011/0076424 A1 | 3/2011 | Pellerite | |
| 2011/0288227 A1 | 11/2011 | Lewandowski | |

FOREIGN PATENT DOCUMENTS

| | | |
|---|---|---|
| EP | 0980682 | 2/2000 |
| EP | 1116769 | 7/2001 |
| EP | 1285947 | 2/2003 |
| EP | 2067797 | 6/2009 |
| GB | 2449926 | 12/2008 |
| JP | 5-98049 | 4/1993 |
| JP | 5-163317 | 6/1993 |
| JP | 6-128501 | 5/1994 |
| JP | 61-36355 | 5/1994 |
| JP | 6-180859 | 6/1994 |
| JP | 07-041528 | 2/1995 |
| JP | 9-268260 | 10/1997 |
| JP | 2002-105058 | 4/2002 |
| JP | 2003-149875 | 5/2003 |
| JP | 2004-006232 | 1/2004 |
| JP | 2004-255481 | 9/2004 |
| JP | 2005-223967 | 8/2005 |
| JP | 2005-255843 | 9/2005 |
| JP | 2006/137885 | 6/2006 |
| JP | 2006-519164 | 8/2006 |
| JP | 2007/308616 | 11/2007 |
| JP | 2007-320093 | 12/2007 |
| JP | 2006-519164 | 8/2008 |
| JP | 2008-285670 | 11/2008 |
| JP | 2009/049397 | 3/2009 |
| JP | 2009-149828 | 7/2009 |
| JP | 2009-173925 | 8/2009 |
| JP | 2009-179671 | 8/2009 |
| JP | 2009-179727 | 8/2009 |
| JP | 2009173925 A * | 8/2009 |
| JP | 2009-209219 | 9/2009 |
| JP | 2009-227949 | 10/2009 |
| JP | 2009-263627 | 11/2009 |
| WO | 97/05182 | 2/1997 |
| WO | 01/30305 | 5/2001 |
| WO | 01/30306 | 5/2001 |
| WO | 01/30307 | 5/2001 |
| WO | 02/055011 | 7/2002 |
| WO | 03/063804 | 8/2003 |
| WO | 2004/069215 | 8/2004 |
| WO | 2006/026064 | 3/2006 |
| WO | 2006/053083 | 5/2006 |
| WO | WO 2006053083 A2 * | 5/2006 |
| WO | 2007/030679 | 3/2007 |
| WO | 2007/030715 | 3/2007 |
| WO | 2008/021533 | 2/2008 |
| WO | 2009/029438 | 3/2009 |
| WO | 2009/134694 | 11/2009 |
| WO | 2010/070819 | 6/2010 |
| WO | 2011/025963 | 3/2011 |
| WO | 2011/031442 | 3/2011 |
| WO | 2011/087621 | 7/2011 |
| WO | 2011/146356 | 11/2011 |

OTHER PUBLICATIONS

Baranyai et al., "Thermal Degradation of Ionic Liquids at Elevated Temperatures", Aust. J. Chem. 2004, 57, 145-147.

Bowyer et al., "Indium-Mediated Addition of 4-Bromocrotonic Acid to Aldehydes and Ketones—A Simple, High Yielding Route to α-Allyl-β-Hydroxy Carboxylic Acids", Aust. J. Chem. 2004, 57, 135-137.

Castner, Jr. et al., "Intermolecular Dynamics, Interactions, and Solvation in Ionic Liquids", Accounts of Chemical Research, 2007, 40, 1217-1227.

Diao et al., "High Performance Cross-Linked Poly(2-acrylamido-2-methylpropanesulfonic acid)-Based Proton Exchange Membranes for Fuel Cells", Macromolecules, vol. 43, Jul. 14, 2010, pp. 6398-6405.

Earle et al., "Keto-Enol Tautomerism as a Polarity Indicator in Ionic Liquids", Aust. J. Chem. 2004, 57, 149-150.

Fainerman-Melnikova et al., "Metal-Ion Recognition-Selective Bulk Membrane Transport of Silver(I) Using Thioether Donor Macrocycles as Ionophores, and X-Ray Structure of the Silver Complex of an $S_4$-Donor Ring", Aust. J. Chem. 2004, 57, 161-166.

Forsyth et al., "Ionic Liquids Based on Imidazolium and Pyrrolidinium Salts of the Tricyanomethanide Anion", Aust. J. Chem. 2004, 57, 121-124.

Forsyth et al., "Ionic Liquids—An Overview", Aust. J. Chem. 2004, 57, 113-119.

Friberg et al. "Copolymerization in a Non-Aqueous Lyotropic Liquid Crystal", Journal of Dispersion Science and Technology, vol. 14, No. 2, Jan. 1, 1993; 205-235.

Friberg et al., "Molecular Location in a Nonaqueous Lyotropic Liquid Crystal Polymer", Journal of Polymer Science, Part A, vol. 28, 1990, pp. 3575-3585.

(56) References Cited

OTHER PUBLICATIONS

Friberg, "Polyelectrolyte Synthesis in a Lamellar Liquid Crystal", Ber. Bundesges. Phys. Chem., vol. 100, No. 6, 1996, pp. 1083-1086.
Gou et al., "Measurement of the Dissolved Oxygen Concentration in Acryalte Monomers with a Novel Photochemical Methods", Journal of Polymer Science, Polym. Sci.: Part A: Polymer Chemistry. vol. 42, (2004), pp. 1285-1292.
Green et al., (2009) "The Design of Polymeric Ionic Liquids for the Preparation of Functional Materials", Polymer Reviews 49: 4, 339-360.
Guest Editorial, "Ionic Liquids", Accounts of Chemical Research, 2007, 40, 1077-1078.
Han et al., "Ionic Liquids in Separations", Accounts of Chemical Research, 2007, 40, 1079-1086.
Hardcare et al., "Structure and Solvation in Ionic Liquids", Accounts of Chemical Research, 2007, 40, 1146-1155.
Hemeon et al., Manganese Dioxide Allylic and Benzylic Oxidation Reactions in Ionic Liquids, Aust. J. Chem. 2004, 57, 125-128.
Hu et al., "Room-Temperature Ionic Liquids: Slow Dynamics, Viscosity, and the Red Edge Effect", Accounts of Chemical Research, 2007, 40, 1097-1105.
Ilesinghe et al., "An Evaluation of Some Hindered Diamines as Chiral Modifiers of Metal-Promoted Reactions", Aust. J. Chem. 2004, 57, 167-176.
Iwata et al., "Local Structure Formation in Alkyl-imidazolium-Based Ionic Liquids as Revealed by Linear and Nonlinear Raman Spectroscopy", Accounts of Chemical Research, 2007, 40, 1174-1181.
Jimenez et al., "Frontal Polymerization with Monofunctional and Difunctional Ionic Liquid Monomers", Journal of Polymer Science: Part A: Polymer Chemistry, vol. 45, 2745-2754 (2007).
Jimenez et al., "Photopolymerization Kinetics of Ionic Liquid Monomers Derived From the Neutralization Reaction Between Trialkylamines and Acid-Containing (Meth)Acrylates", Journal of Polymer Science: Part A: Polyer Chemistry, pp. 3009-3021 (Dec. 2006/Feb. 2007).
Juger et al., "Synthesis, Polymerization and Conducting Properties of an Ionic Liquid-Type Anionic Monomer", Tatrahedron Letters 50 (2009) 128-131.
Kapakoglou et al., "Coacervation of Surface-Functionalized Polymerized Vesicles Derived from Ammonium Bromide Surfactants. Application to the Selective Speciation of Chromium in Environmental Samples", Anal. Chem., vol. 80, 2008, pp. 9787-9796.
Klee et al., "Monomers for low shrinking composites, $2^a$—Synthesis of branched methacrylates and their application in dental composites," Macromolecular Chemistry and Physics, vol. 200, Issue 3, pp. 517-523, (1999).
Lu et al., "Advanced Applications of Ionic Liquids in Polymer Science", Progress in Polymer Science 34, (2009), 431-448.
Lynden-Bell et al., "Simulations of Ionic Liquids, Solutions, and Surfaces", Accounts of Chemical Research, 2007, 40, 1138-1145.
MacFarlane et al., "Ionic Liquids in Electrochemical Devices and Processes: Managing Interfacial Electrochemistry", Accounts of Chemical Research, 2007, 40, 1165-1173.
Maginn, "Atomistic Simulation of the Thermodynamic and Transport Properties of Ionic Liquids", Accounts of Chemical Research, 2007, 40, 1200-1207.
Mathis et al. "Properties of a New Glass Ionomer/Composite Resin Hybrid Restorative", Abstract No. 51, J. Dent. Res., 66:113 (1987).
Matijevic, Surface & Colloid Science, vol. 6 ed., Wiley Interscience (1973), pp. 23-29.
Meindersma et al., "Ionic Liquids", Ullmann's Encyclopedia of Industrial Chemistry, 2007.
Mosmuller et al., "Lipase Activity in Vesicular Systems: Characterization of *Candida cylindracea* Lipase and Its Activity in Polymerizable Dialkylammonium Surfactant Vesicles", Biotechnology and Boiengineering, vol. 42, 1993, 196-204.
Nakajima, "Preparation of Termally Stable Polymer Electrolytes From Imidazolium-Type Ionic Liquid Derivatives", Science Direct, Polymer 46 (2005) 11499-11504.
Ohno et al., "Amino Acid Ionic Liquids", Accounts of Chemical Research 2007, 40, 1122-1129.
Ohno et al., "Development of new class of ion conductive polymers based on ionic liquids", Electrochimica Acta, vol. 50, No. 2-3, Nov. 30, 2004, pp. 254-260.
Olivier-Bourbigou et al.; "Ionic Liquids and Catalysis: Recent Progress From Knowledge to Applications", Applied Catalysis A: General 373 (2010) 1-56.
Padua et al., Molecular Solutes in Ionic Liquids: A Structural Perspective, Accounts of Chemical Research, 2007, 40, 1087-1096.
Plechkova et al., "Applications of ionic liquids in the chemical industry", Chemical Society Reviews, 2008, 37, pp. 123-150.
Popolo et al., "Clusters, Liquids and Crystals of Dialkyimidazolium Salts. A Combined Perspective from ab Initio and Classical Computer Simulations", Accounts of Chemical Research, 2007, 40, 1156-1164.
Rebelo et al., "Accounting for the Unique Double Dual Nature of Ionic Liquids from a Molecular Thermodynamic and Modeling Standpoint", Accounts of Chemical Research, 2007, 40, 1114-1121.
Ruckenstein et al., "Binding Catalytic Sites to the Surface of Porous Polymers and Some Catalytic Application", Chem. Mater. 1992, vol. 4, pp. 122-127.
Shim et al., "Solvation, Solute Rotation and Vibration Relaxation, and Electrom-Transfer Reactions in Room-Temperature Ionic Liquids", Accounts of Chemical Research 2007, 40, 1130-1137.
Smiglak et al., "The Second Evolution of Ionic Liquids: From Solvents and Separations to Advanced Materials-Energetic Examples From the Ionic Liquid Cookbook", Accounts of Chemical Research 2007, 40, 1182-1192.
Soulivong et al., "A Long-Chain Phosphine Designed as a Metallomesogen Generator-Synthesis and Coordination Properties", Aust. J. Chem. 2004, 57, 157-160.
Tan et al., "Photopolymerization and Characteristics of Reactive Organoclay-Polyurethane Nanocomposites", Polymer Composites, vol. 30, No. 5, Oct. 20, 2008, pp. 612-618.
Torimoto et al., "New Frontiers in Materials Science Opened by Ionic Liquids", Adv. Mater. 2009, 21, 1-26.
Tundo et al., Functionally Polymerized Surfactant Vesicles. Synthesis and Characterization, J. Am. Chem. Soc., vol. 104, 1982, pp. 456-461.
Vijayaraghavan et al., "Charge Transfer Polymerization in Ionic Liquids", Aust. J. Chem. 2004, 57, 129-133.
Wang et al., "Understanding Ionic Liquids through Atomistic and Coarse-Grained Molecular Dynamics Simulations", Accounts of Chemical Research, 2007, 40, 1193-1199.
Watts et al., "Determination of Polymerization Shrinkage Kinetics in Visible Light-Cured Materials: Methods Development", Dental Materials Oct. 1991, pp. 281-286.
Whitehead et al., "Analysis of Gold in Solutions Containing Ionic Liquids by Inductively Coupled Plasma Atomic Emission Spectrometry", Aust. J. Chem. 2004, 57, 151-155.
Yoshizawa et al., "Design of Ionic Liquids for Electrochemical Applications", Aust. J. Chem. 2004, 57, 139-144.
Yoshizawa et al., "Novel Polymer Electrolytes Prepared by Copolymerization of Ionic Liquid Monomers", Polymers for Advanced Technologies 13, 589-594 (2002).
Zaderenko, et al., "Synthesis and Regioselective Hydrolysis of 2-Imidazol-1-ylsuccinic Esters," Journal of Organic Chemistry, vol. 59, Issue 21, pp. 6268-6273, (1994).
The Dental Advisor; 3M ESPE Filtek™ Z250 Universal Restorative 9-year Clinical Performance+++++; Jun. 2008, 2 pages.
International Search Report PCT/US2010/046720 Jun. 16, 2011, 7 pgs.
Ohno, "Design of Ion Conductive Polymers Based on Ionic Liquids", Macromol. Symp. 2007, pp. 551-556.
Antonucci et al., "Synthesis, Characterization and Evalutaion of Novel, Anti-Bacterial Monomers for Dental and Biomedical Applications", vol. 50, No. 2, Aug. 16, 2009, pp. 132-133, [[retrieved from the internet]] <http://www.nist.gov/manuscript-publication-search.cfm?pub_id=901947>.

\* cited by examiner

COMPOSITIONS AND ARTICLES COMPRISING POLYMERIZABLE IONIC LIQUID MIXTURE, AND METHODS OF CURING

CROSS REFERENCE TO RELATED APPLICATIONS

This application is a national stage filing under 35 U.S.C. 371 of PCT/US2010/046720, filed 26 Aug. 2010, which claims priority to U.S. Provisional Application No. 61/237,992, filed 28 Aug. 2009; U.S. Provisional Application No. 61/289,169, filed 22 Dec. 2009; and U.S. Provisional Application No. 61/360,185, filed 30 Jun. 2010, the disclosure of which is incorporated by reference in their entirety herein.

BACKGROUND

Ionic liquids (ILs) are salts in which the cation and anion are poorly coordinated. At least one of the ionic components is organic and one of the ions has a delocalized charge. This prevents the formation of a stable crystal lattice, and results in such materials existing as liquids, often at room temperature, and at least, by definition, at less than 100° C. For example, sodium chloride, a typical ionic salt, has a melting point of about 800° C., whereas the ionic liquid N-methylimidazolium chloride has a melting point of about 75° C.

Ionic liquids typically comprise an organic cation, such as a substituted ammonium or a nitrogen-containing heterocycle, such as a substituted imidazolium, coupled with an inorganic anion. However, species have also been described wherein the cation and anion are organic. When the ionic liquid comprises at least one polymerizable group, such ionic liquid is a polymerizable ionic liquid ("PIL").

SUMMARY

Presently described are curable compositions comprising a mixture of at least one (e.g. free-radically) polymerizable ionic liquid and at least one other ethylenically unsaturated monomer, oligomer, or polymer. The polymerizable ionic liquid is characterized as having an air to nitrogen curing exotherm ratio of at least 0.70. In some embodiments, the air to nitrogen curing exotherm ratio of the polymerizable ionic liquid is at least 0.75, 0.80, 0.85, 0.90, or 0.95. The other ethylenically unsaturated monomer, oligomer, or polymer typically has a substantially lower air to nitrogen curing exotherm ratio, e.g. no greater than about 0.50. The curable compositions typically comprise an initiator, such as a photoinitiator.

The presence of the polymerizable ionic liquid improves the curing of the composition especially in the presence of oxygen (e.g. air) without inerting with a gas such as nitrogen or curing between oxygen impermeable films. The presence of the other ethylenically unsaturated monomer, oligomer, or polymer can improve the stability of the polymerizable ionic liquid by hindering unintended polymerization, such as during storage. The presence of the polymerizable ionic liquid may also improve the cure speed of the polymerizable composition, may require reduced amounts of initiators and/or require reduced light intensity while curing effectively in the presence of oxygen. This ca provide cured (e.g. coating) materials with faster, lower cost compositions and processes.

In some favored embodiments, the curable composition comprises a multifunctional polymerizable ionic liquid comprising at least two ethylenically unsaturated groups, optionally in combination with a monofunctional polymerizable ionic liquid. One favored multifunctional polymerizable ionic liquid comprises at least two ethylenically unsaturated groups, each bonded to the cationic group via a divalent non-alkylene linking group. Other favored multifunctional polymerizable ionic liquids comprise a polymerizable anion and a polymerizable cation. In one embodiment, the polymerizable cation comprises an aromatic moiety. In another embodiment, the polymerizable anion comprises an aromatic moiety, such as an aromatic carboxylate anion.

In another embodiment, a monofunctional polymerizable ionic liquid is described comprising a non-polymerizable imidazolium cation and a (e.g. non-fluorinated) sulfonate anion, such as

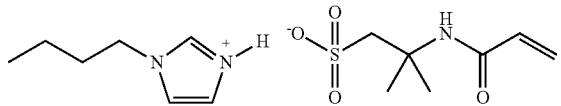

In other embodiments, articles are described such as a coated substrate comprising a substrate and a cured coating of the composition described herein on a surface of the substrate.

In other embodiments, methods of making articles from the curable composition described herein are described.

DETAILED DESCRIPTION

As used herein, "hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked).

As used herein, the term "(meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof. As used herein, "a," "an," "the," "at least one," and "one or more" are used interchangeably.

Unless specified otherwise, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

Unless specified otherwise, "heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like.

Unless otherwise noted, heteroalkyl groups may be mono- or polyvalent.

Unless specified otherwise, "aromatic group" or "aromatic moiety" includes 6-18 ring atoms and can contain optional fused rings, which may be saturated or unsaturated. Examples of aromatic groups include phenyl, naphthyl, biphenyl, phenanthryl, and anthracyl. The aromatic group may optionally contain 1-3 heteroatoms such as nitrogen, oxygen, or sulfur and can contain fused rings. Examples of aromatic group having heteroatoms include pyridyl, furanyl, pyrrolyl, thienyl, thiazolyl, oxazolyl, imidazolyl, indolyl, benzofuranyl, and benzthiazolyl. Unless otherwise noted the aromatic group may be mono- or polyvalent.

Also herein, the recitations of numerical ranges by endpoints include all numbers subsumed within that range (e.g., 1 to 5 includes 1, 1.5, 2, 2.75, 3, 3.80, 4, 5, etc.).

Presently described are various curable compositions that comprise a polymerizable ionic liquid, comprising a cation and anion that are poorly coordinated. Such polymerizable ionic liquids have a melting point ($T_m$) below about 100° C. The melting point of these compounds is more preferably below about 60° C., 50° C., 40° C., or 30° C. and most preferably below about 25° C., for ease of use in various polymerizable compositions as described herein with or without the aid of solvent carriers in the composition. Polymerizable ionic liquids having a melting point below 25° C. are liquids at ambient temperature. As the molecular weight of the polymerizable ionic liquid increases, the viscosity can increase. In some embodiments, the molecular weight of the polymerizable ionic liquid is less than 1000 g/mole.

Suitable cationic groups, also known as onium salts, include substituted ammonium salts, substituted phosphonium salts, substituted pyridinium salts, and substituted imidazolium salts. The structures of the cations of such onium salts are depicted as follows:

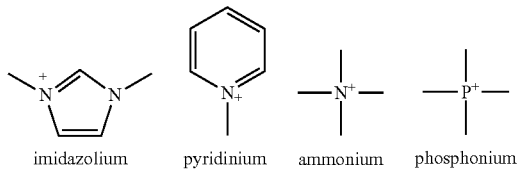

imidazolium    pyridinium    ammonium    phosphonium

Other cationic groups include pyrazolium, pyrrolidinium, and cholinium.

The anion may be organic or inorganic, and is typically a monovalent anion, i.e. having a charge of −1. Illustrative examples of anions useful herein include various organic anions such as carboxylates ($CH_3CO_2^-$, $C_2H_5CO_2^-$, $ArCO_2^-$), sulfates ($HSO_4^-$, $CH_3SO_4^-$), sulfonates ($CH_3SO_3^-$), tosylates, and fluoroorganics ($CF_3SO_4^-$, $(CF_3SO_2)_2N^-$, $(C_2F_5SO_2)_2N^-$, $(C_2F_5SO_2)(CF_3SO_2)N^-$, $CF_3CO_2^-$, $CF_3C_6F_4SO_3^-$, $CH_3C_6F_4SO_3^-$, tetrakis(pentafluorophenyl)borate).

In some embodiments, curable (e.g. dental) compositions are described comprising a polymerizable ionic liquid comprising an aromatic carboxylate anion $ArCO_2^-$. Such polymerizable ionic liquids may comprise a (e.g. free-radically) polymerizable anion, a (e.g. free-radically) polymerizable cation, or both a (e.g. free-radically) polymerizable anion and a (e.g. free-radically) polymerizable cation. In some embodiments, the cation is a substituted ammonium, phosphonium, or imidazolium cation.

The anion may alternatively be an inorganic anion such as $ClO_4^-$, fluoroinorganics ($PF_6^-$, $BF_4^-$, $AsF_6^-$, $SbF_6^-$) and halides ($Br^-$, $I^-$, $Cl^-$). In some embodiments, the anion is preferably an organic anion such as a sulfonate. Organic anions may be non-halogenated which is amenable to providing (e.g. dental) compositions that are halogen-free. In some embodiments, the (e.g. sulfonate) anion is non-fluorinated and lacks an aromatic substituent. Further, in some embodiments, the anion lacks ethylenically unsaturated groups and thus is a non-polymerizable anion. In other embodiments, the organic anion is polymerizable.

The polymerizable groups are ethylenically unsaturated terminal polymerizable groups. The ethylenically unsaturated groups are preferably free-radically polymerizable groups including (meth)acryl such as (meth)acrylamide ($H_2C=CHCON-$ and $H_2C=CH(CH_3)CON-$) and (meth)acrylate ($CH_2CHCOO-$ and $CH_2C(CH_3)COO-$). Other ethylenically unsaturated (e.g. free-radically) polymerizable groups include vinyl ($H_2C=C-$) including vinyl ethers ($H_2C=CHOCH-$). The methacrylate functional onium salts are typically preferred over the acrylate onium salts in compositions because they exhibit a slower rate of cure.

The polymerizable ionic liquid functions as a reactive monomer and thus is substantially unpolymerized in the curable composition at the time the curable composition is applied to a substrate or formed into a (e.g. dental) article, such as a dental crown. Hence, the curable composition hardens upon curing via polymerization of the ethylenically unsaturated groups of the (e.g. multifunctional) polymerizable ionic liquid. Such curing generally results in a permanent bond. For example, when the curable composition is an adhesive, the bonded substrate typically cannot be separated without substrate damage.

In some favored embodiments, the polymerizable ionic liquid is sufficiently low in viscosity that it acts as a reactive diluent. In such embodiment, the composition can advantageously be substantially free of solvents, especially organic solvents. This can result in increased efficiency with respect to manufacturing time as well as energy consumption by reducing or eliminating drying the composition prior to curing. This can also reduce the volatile organic content (VOC) emissions of the composition.

In some embodiments, the polymerizable ionic liquid is monofunctional, having one polymerizable ethylenically unsaturated group. Monofunctional polymerizable ionic liquids can be combined with conventional multifunctional ethylenically unsaturated (e.g. (meth)acrylate) monomers to enhance curing thereby minimizing the formation of a surface residue surmised to be caused by oxygen curing inhibition of curable compositions.

In other embodiments, the polymerizable ionic liquid is multifunctional, typically comprising two or three polymerizable groups. For example, in some embodiments the polymerizable ionic liquid may comprise a polymerizable cation and a polymerizable anion. In other embodiments, the multifunctional polymerizable ionic liquids described herein can be characterized as having a multifunctional cation, having two, three, or more polymerizable groups bonded to the same cationic group.

In some embodiments, the polymerizable ionic liquid is a mixture comprising at least one multifunctional polymerizable ionic liquid and at least one monofunctional polymerizable ionic liquid.

The polymerizable ionic liquid(s) is typically employed in combination with other conventional (e.g. (meth)acrylate) ethylenically unsaturated monomer(s), oligomer(s), or polymer(s). By "other" is it meant an ethylenically unsaturated monomer that is not a polymerizable ionic liquid. Although conventional monomers are polymerizable and many are liquids at 25° C., conventional monomers are typically nonionic, lacking a cation and an anion.

It has been found that a polymerizable ionic liquid can be used in place of conventional hardenable (meth)acrylate monomers, such as 2-hydroxyethyl methacrylate (HEMA), triethyleneglycol dimethacrylate (TEGDMA), and 2,2-bis[4-(2-hydroxy-3-methacyloxypropoxy)phenyl]propane (BisGMA), such as commonly used in curable (e.g. dental) compositions. Such embodiment is amenable to providing a dental composition that is free of monomer derived from bisphenol A (such as BisGMA).

Preferred (e.g. multifunctional) polymerizable ionic liquids exhibit a high air to nitrogen curing exotherm ratio, as can be measured by photo DSC according to the test method described in the examples. The air to nitrogen curing ratio is typically at least 0.70 or 0.75. In preferred embodiments, the air to nitrogen curing exotherm ratio is typically at least the 0.80, 0.85, 0.90, or 0.95. For embodiments wherein the air to nitrogen curing ratio of the polymerizable ionic liquid is sufficiently high, the polymerizable ionic liquid can advantageously be substantially completely cured in air (i.e. an oxygen rich environment) rather than requiring curing in the absence of oxygen.

A completely cured (i.e. hardened) polymerizable ionic liquid is solid at 25° C. and is substantially free of uncured polymerizable ionic liquid. When significant uncured polymerizable ionic liquid is present it typically results as a surface residue exhibiting a "wet" appearance. Minimal surface inhibition not only provides more complete curing but also minimizes the formation of a less cured oxygen inhibited surface layer. This provides the benefit of reduced extractables and also less need to remove the uncured "wet" monomer layer by use of an absorbant wiping material with or without a solvent such as ethanol. The extent of curing can be determined by various methods known in art. One common method is to determine the amount of uncured material by solvent extraction. In preferred embodiments, the amount of uncured extractable polymerizable ionic liquid is less than 10%, more preferably less than 5%, and most preferably less than 1% by weight of the cured composition.

Conventional (meth)acrylate monomers typically have an air to nitrogen curing exotherm ratio of no greater than 0.50, 0.40, 0.35, 0.20, or 0.25 or lower. For example, TEGMA has been found to have an air to nitrogen curing exotherm ratio of about 0.36; whereas HEMA has been found to have an air to nitrogen curing exotherm ratio of less than 0.25. Although the photocuring of conventional (meth)acrylate monomers and especially methacrylate monomers is typically inhibited by oxygen present in air, the inclusion of the (e.g. multifunctional) polymerizable ionic liquid can sufficiently increase the air to nitrogen curing exotherm of the mixture such that the mixture can advantageously be substantially completely cured in air. For embodiments wherein the composition is to be cured in air and the multifunctional polymerizable ionic liquid is combined with another polymerizable (meth)acrylate component that exhibits a lower air to nitrogen curing exotherm ratio, the air to oxygen curing exotherm ratio of the (e.g. multifunctional) polymerizable ionic liquid, described herein, is preferably at least 0.85, 0.90, or 0.95.

The total concentration of (e.g. multifunctional) polymerizable ionic liquid(s) having a high air to nitrogen curing exotherm ratio, is typically at least 30 wt-% and preferably at least 40 wt-% of the unfilled composition (the total polymerizable organic composition excluding inorganic filler). In this embodiment, the total concentration of other ethylenically unsaturated (e.g. (meth)acrylate) monomer(s), oligomer(s), and polymer(s)) is typically at least 10 wt-%, 20 wt-%, 30 wt-%, 40 wt-%, 50 wt-%, or 65 wt-%.

Although the presence of the (e.g. multifunctional) polymerizable ionic liquid having a high air to oxygen curing ratio is beneficial to curing, as just described, the presence of the other conventional (meth)acrylate monomer may also benefit the (e.g. multifunctional) polymerizable ionic liquid by improving the stability by hindering unintended polymerization, such as during storage, prior to (e.g. photo) curing. This is amenable to providing one-part curable coating composition. Thus, in at least some favored embodiments the amount of other ethylenically unsaturated (e.g. (meth)acrylate) monomer(s), oligomer(s) is typically at least 21 wt-%, 22 wt-%, 23 wt-%, 24 wt-%, or 25 wt-% of the unfilled composition. Thus, the concentration of (e.g. multifunctional) polymerizable ionic liquid(s) having a high air to oxygen curing ratio is less than 80 wt-%. Typically, it is preferred to maximize the concentration of other ethylenically unsaturated (e.g. (meth)acrylate) monomer(s), oligomer(s) provided that the air to oxygen curing ratio of the mixture is at least 0.75 and preferably at least 0.80, 0.85, 0.90 or greater. Depending on the selection of other ethylenically unsaturated (e.g. (meth) acrylate) monomer(s), oligomer(s), this concurrently can be achieved with when the concentration of (e.g. multifunctional) polymerizable ionic liquid(s) having a high air to oxygen curing ratio is at least about 35 wt-%, 40 wt-%, or 45 wt-%. For embodiments, wherein the other ethylenically unsaturated monomer(s), oligomer(s), and polymer(s) has an air to oxygen curing exotherm of about 0.25 or lower, the concentration of polymerizable ionic liquid is preferably at least 50 wt-%, 55 wt-%, or 60 wt-%.

In some favored embodiments, the curable compositions comprise a new class or new species of polymerizable ionic liquid.

In some favored embodiments the curable composition comprises a multifunctional cation, having two or more polymerizable groups, each bonded to the same cationic group via a divalent non-alkylene linking group. Such multifunctional polymerizable ionic liquid is further described in U.S. Provisional Application Ser. No. 61/237,992, titled, "OPTICAL DEVICE WITH ANTISTATIC COATING" and U.S. Provisional Application Ser. No. 61/289,072, titled, "POLYMERIZABLE IONIC LIQUID COMPRISING MULTIFUNCTIONAL CATION AND ANTISTATIC COATINGS"; incorporated herein by reference. As used herein, linking groups refer to the entirety of the chain of atoms between the (e.g. single) cation and ethylenically unsaturated terminal group. Although the linking groups may and often comprises lower alkylene segments, e.g. of 1 to 4 carbon atoms, the linking groups further comprise other atoms within the carbon backbone and/or other groups pendant to the (e.g. carbon) backbone. Most commonly, the linking groups comprise heteroatoms such as sulfur, oxygen, or nitrogen, and more commonly oxygen or nitrogen. The linking groups may comprise linkages such as amide (—CONR—) or ether (—COC—) linkages and more commonly urethane (—ROCONR—), urea (—RNCONR—), or ester linkages (—COOR—); wherein R is a lower alkyl of 1-4 carbon atoms.

For embodiments wherein the cation is ammonium or phosphonium, the polymerizable ionic liquid may have the general formula:

$$X^- \quad [R^2-L^1\!\!-\!\!\!{}_m Q^+\!\!-\!\!\!{}_{\phantom{m}} R^1]_n$$

wherein:
Q is nitrogen or phosphorous;
$R^1$ is independently hydrogen, alkyl, aryl, alkaryl, or a combination thereof;
$R^2$ is independently an ethylenically unsaturated group;
$L^1$ is independently a linking group with the proviso that at least two of the linking groups are not alkylene linking groups;
m is an integer of 2 to 4;
n is an integer of 0 to 2;
and m+n=4; and
X is an anion.

At least two of the linking groups, $L^1$, are preferably linking groups that comprise one or more heteroatoms such as nitrogen, oxygen, or sulfur. In favored embodiments, at least two of the linking groups, $L^1$ comprise nitrogen or oxygen heteroatoms, such as linking groups that comprise an amide, urea, ether, urethane or ester linkage. The linking group may comprise more than one of such linkages.

Although each terminal ethylenically unsaturated group, $R^2$, bonded to each linking group can comprise a different ethylenically unsaturated group, the terminal ethylenically unsaturated group, $R^2$, is typically the same ethylenically unsaturated polymerizable group, such as the same vinyl, (meth)acrylamide, or (meth)acrylate group.

In some embodiments, m is 3 and thus, the polymerizable ionic liquid is a trifunctional (e.g. tri(meth)acrylate) polymerizable ionic liquid. In other embodiments, m is 2 and thus, the polymerizable ionic liquid is a difunctional (e.g. di(meth)acrylate) polymerizable ionic liquid.

In some embodiments, n is at least 1. $R^1$ is typically hydrogen or a straight-chain lower alkyl of 1 to 4 carbon atoms. However, $R^1$ may optionally be branched or comprise a cyclic structure. $R^1$ may optionally comprise phosphorous, halogen, or one or more heteroatoms such as nitrogen, oxygen, or sulfur.

Preferred polymerizable ionic species wherein the cation is ammonium include:

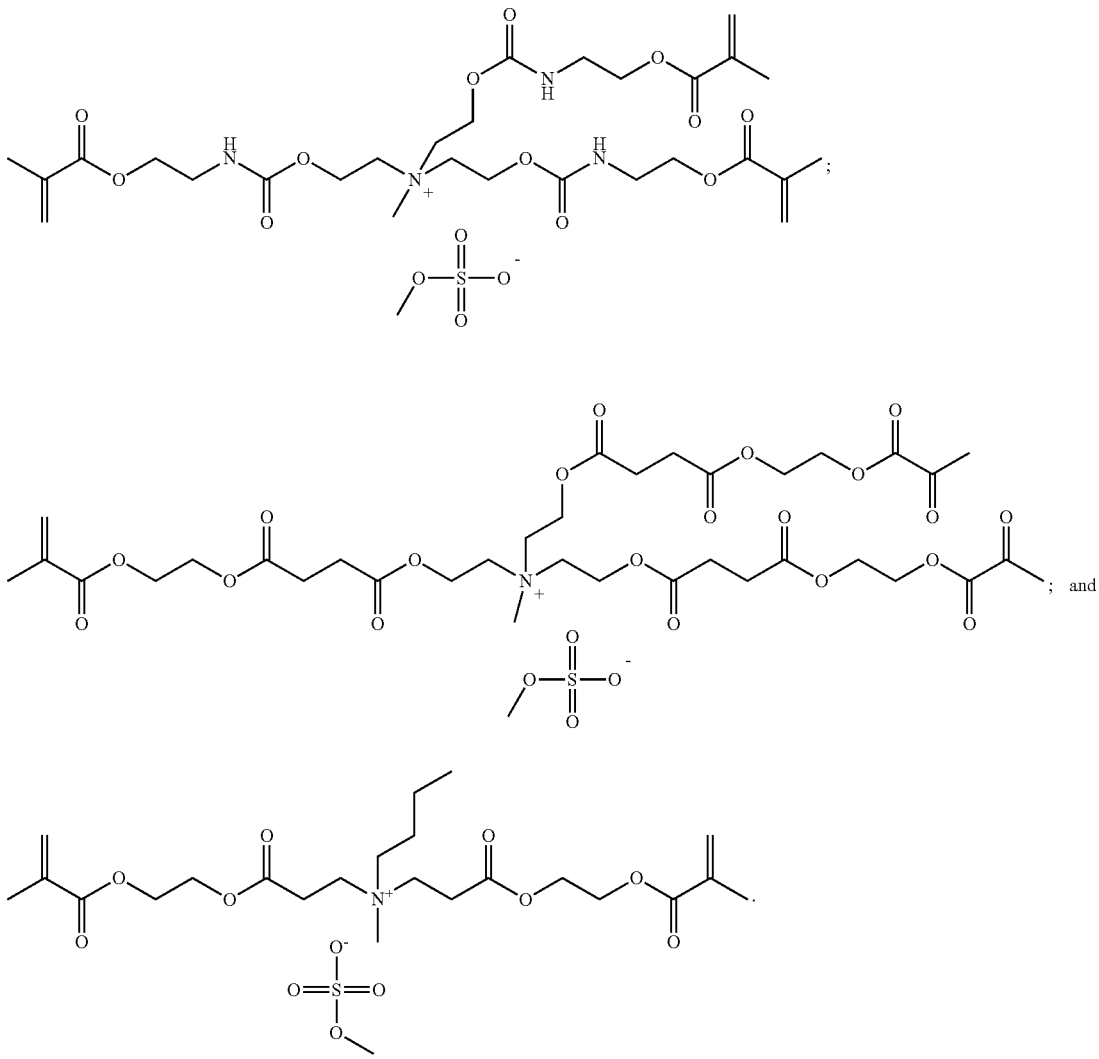

These species just described can include various other anions, as previously described.

When such polymerizable ionic liquid is utilized in an antistatic coating, the polymerizable ionic liquid (i.e. onium salt) may be present in the antistatic layer at a weight percentage of 1 to 99.5%, preferably 10 to 60%, and more preferably 30 to 50%. For this embodiment, the acryl functional polymerizable ionic liquids are preferred over the methacryl polymerizable ionic liquid because they exhibit a faster and greater degree of cure.

In other embodiments, the polymerizable composition comprises an ionic liquid comprising a polymerizable cation and a polymerizable anion. In one embodiment, the polymerizable cation comprises an aromatic moiety. The polymerizable anion is preferably a carboxylate anion such as an aromatic carboxylate anion.

Such polymerizable ionic liquids may comprise a substituted ammonium cation. The polymerizable ionic liquid may have the general formula:

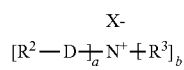

wherein
$R^3$ is independently hydrogen or a C2-C8 alkyl group;
$R^2$ is an ethylenically unsaturated group;
D is a divalent linking group comprising an aromatic moiety;
a is 1-4;
b is 0-3;
a+b=4; and
$X^-$ is an organic cation comprising at least one ethylenically unsaturated group.

The ethylenically unsaturated group may be a vinyl group.
Some illustrative species include

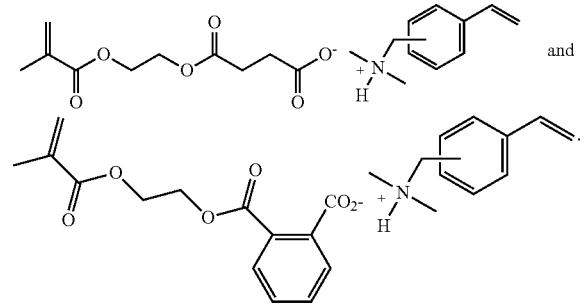

In another favored embodiment, the polymerizable composition comprises a polymerizable ionic liquid comprising an aromatic carboxylate anion.

Such (e.g. free-radically) polymerizable ionic liquids may have the general formula:

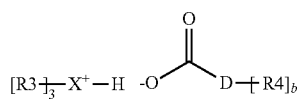

wherein
X is nitrogen or phosphorus;
R3 and R4 are independently alkyl or heteroalkyl, and at least one R3 or R4 comprises a free-radically polymerizable group;

D comprises an aromatic moiety and optionally comprises a linking group between the carboxylate end group and aromatic moiety and/or optionally comprises a linking group between the aromatic moiety and R4; and
b is 0-2.

The free-radically polymerizable groups are preferably (meth)acrylate groups. The aromatic moiety of D typically comprises one, two, or three aromatic rings that are optionally fused, such as in the case of phthalate or aromatic rings derived from biphenyl or triphenyl compounds.

In some embodiments, both the substituted (e.g. ammonium) cation and the aromatic carboxylate anion each comprise at least one free radically polymerizable group, such as (meth)acrylate groups. In some embodiments, two R3 are alkyl groups and one R3 group comprises a (meth)acrylate group. In another embodiment, two R3 are alkyl groups and one R3 group comprises an aromatic (e.g. phenyl) (meth) acrylate group. The alkyl groups of R3 typically comprise at least one carbon atom (e.g. methyl) and no greater than 8, or no greater than 6, or no greater than 4 carbon atoms. A linking group is typically present between the terminal (e.g. free-radically) polymerizable (meth)acrylate group and the (e.g. ammonium) cation ($X^+$), a previously described. D may comprise a divalent (e.g. ester) linking group between a (e.g. phenyl) aromatic group and terminal (meth)acrylate group.

Examples of such free-radically polymerizable ionic liquids include:

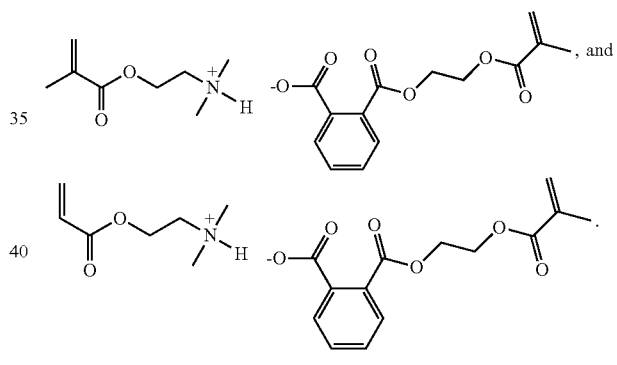

In another favored embodiment, the composition comprises a monofunctional polymerizable ionic liquid comprising a non-polymerizable cation, such as a substituted imidazolium cation and a polymerizable anion. The imidazolium cation is typically substituted with one or two lower alkyl groups of 1 to 4 carbon atoms. The anion is preferably a (e.g. nonfluorinated) sulfonate anion. One favored species is

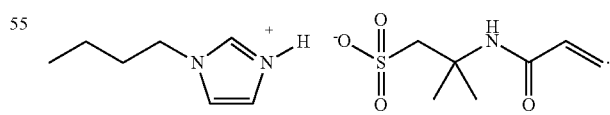

The species described herein can include various other anions, as previously described.

The polymerizable ionic liquids described herein can be made by several methods. One method includes reaction of a hydroxyl functional ionic precursor with a polymerizable isocyanate such as depicted by the following reaction scheme:

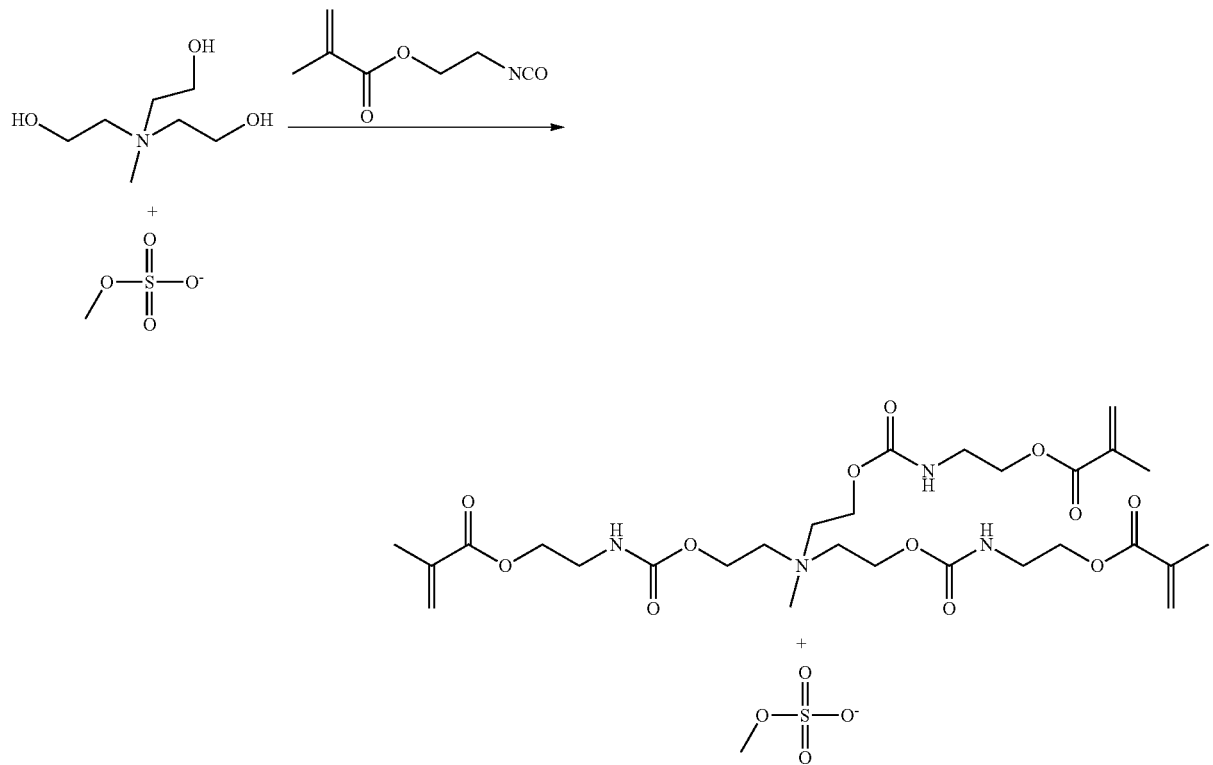

Commercially available starting materials include tris-(2-hydroxyethyl)-methyl ammonium methyl sulfate available from BASF (BASIONIC FS01), diethanolamine hydrochloride, 2-amino-1,3-propanediol hydrochloride, and tris(hydroxymethyl)aminomethane hydrochloride. The ionic product may be further reacted to exchange the anion using anion metathesis as described in "Ionic Liquids", Meindersma, G. W., Maase, M., and De Haan, A. B., Ullmann's Encyclopedia of Industrial Chemistry, 2007.

Another method includes the reaction of a hydroxyl functional amine precursor with a polymerizable isocyanate, followed by alkylation or acidification, such as depicted by the following reaction scheme:

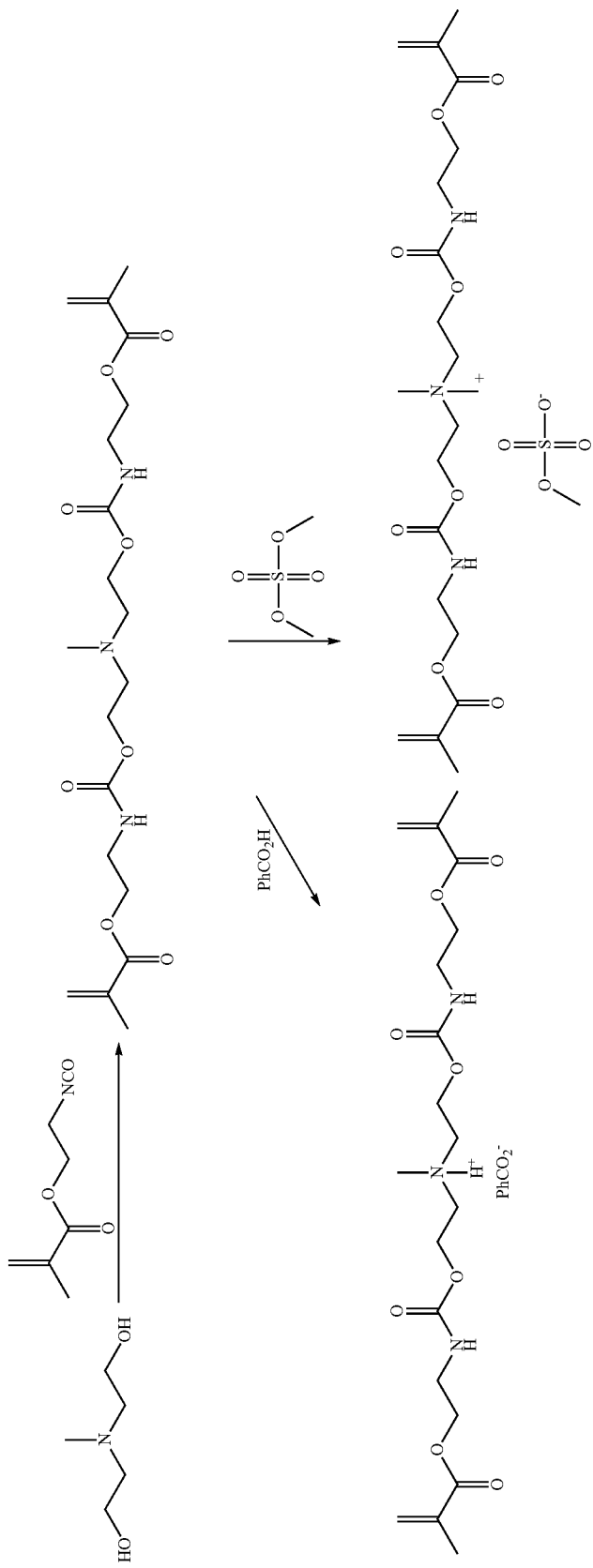

Commercially available starting materials include diethanol amine, diisopropanol amine, N-methyldiethanol amine, N-ethyldiethanol amine, N-butyldiethanol amine, triethanol amine, 1-[N,N-bis(2-hydroxyethyl)-amino]-2-propanol, triisopropanol amine, 3-amino-1,2-propanediol, 3-(dimethylamino)-1,2-propanediol, 3-(diethylamino)-1,2-propanediol, 3-(dipropylamino)-1,2-propanediol, 3-(diisopropylamino)1,2,-propanediol, 2-amino-1,3-propanediol, 2-amino-2-ethyl-1,3,-propanediol, 2-amino-2-methyl-1,3,-propanediol, tris(hydroxymethyl)amino methane, bis(2-hydroxyethyl)amino-tris(hydroxymethyl)methane, 2,2-bis(hydroxymethyl)-2,2',2"-nitrilotriethanol, N,N' bis(2-hydroxyethyl)-ethylenediamine, N—N—N'—N'-tetrakis(2-hydroxypropyl)-ethylenediamine, 1,3-bis[tris(hydroxymethyl)-methylamino]propane, 3-pyrrolidino-1,2-propanediol, 3-piperidino-1,2-propanediol, and 1,4-bis(2-hydroxyethyl)-piperazine.

Useful alkylating agents include alkyl halides, sulfates, and phosphonate esters, such as methyl iodide, ethyl iodide, methyl bromide, ethyl bromide, dimethyl sulfate, diethyl sulfate, and dimethyl methylphosphonate. Useful acidification agents include carboxylic acids, organosulfonic acids, and organophosphonic acids and inorganic acids such as hydrochloric acid, hydrofluoric acid, hydrobromic acid, phosphoric acid, nitric acid and the like.

Another method includes the reaction of an amine with an acrylate compound to give a polymerizable amine precursor, followed by alkylation or acidification, such as depicted by the following reaction scheme:

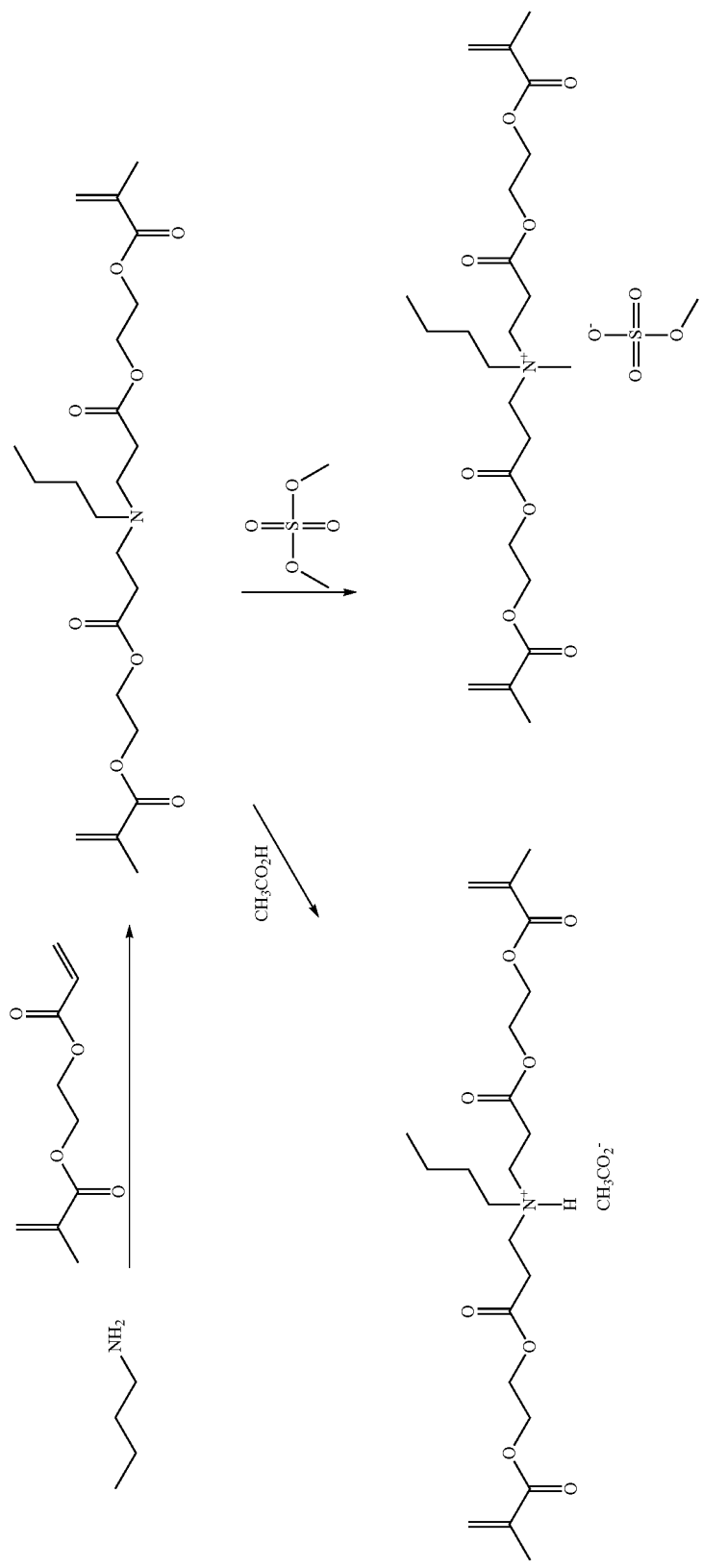

Commercially available starting materials include amines such as methylamine, ethylamine, propylamine, butylamine, hexylamine, isopropylamine, isobutylamine, 1-methylbutylamine, 1-ethyl propylamine, 2-methylbutylamine, isoamylamine, 1,2-dimethylpropylamine, 1,3-dimethylbutylamine, 3,3-dimethylbutylamine, 2-aminoheptane, 3-aminoheptane, 1-methylheptyamine, 2-ethylhexylamine, 1,5-dimethylhexylamine, cyclopropylamine, cyclohexylamine, cyclobutylamine, cyclopentylamine, cycloheptylamine, cyclooctylamine, 2-aminonorbornane, 1-adamantanamine, allylamine, tetrahydrofurfurylamine, ethanolamine, 3-amino-1-propanol, 2-(2-aminoethoxy)ethanol, benzylamine, phenethylamine, 3-phenyl-1-propylamine, 1-aminoindan, ethylenediamine, diaminopropane, and hexamethylenediamine.

Another method, that provides a polymerizable ionic liquid containing an ether linking group, includes the reaction of a hydroxyl functional precursor with a functionalized (meth)acrylate molecule such as depicted by the following reaction scheme:

Another method, that provides a polymerizable ionic liquid containing an amide linking group, includes the reaction of an amine functional precursor with a functionalized (meth)acrylate molecule such as depicted by the following reaction scheme:

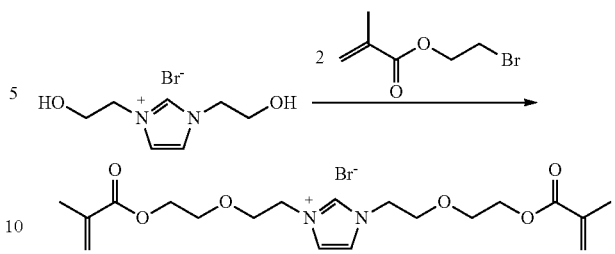

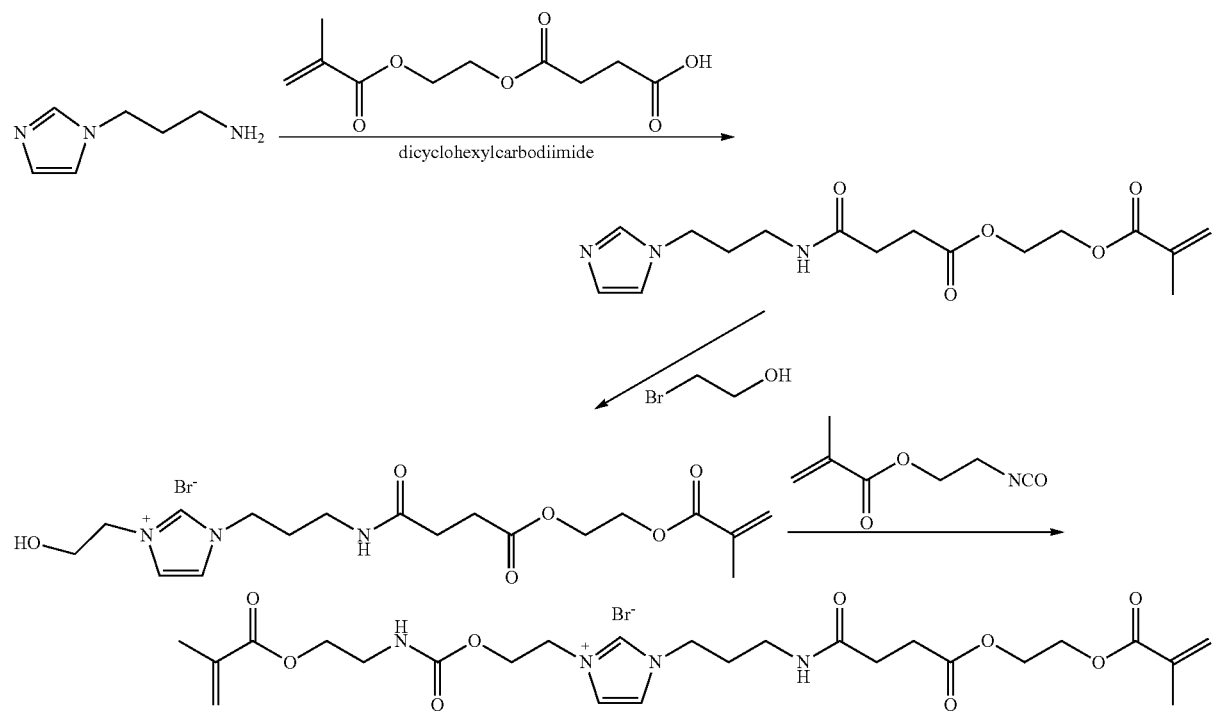

Another illustrative method, that provides a polymerizable ionic liquid containing a urea linking group, is depicted by the following reaction scheme:

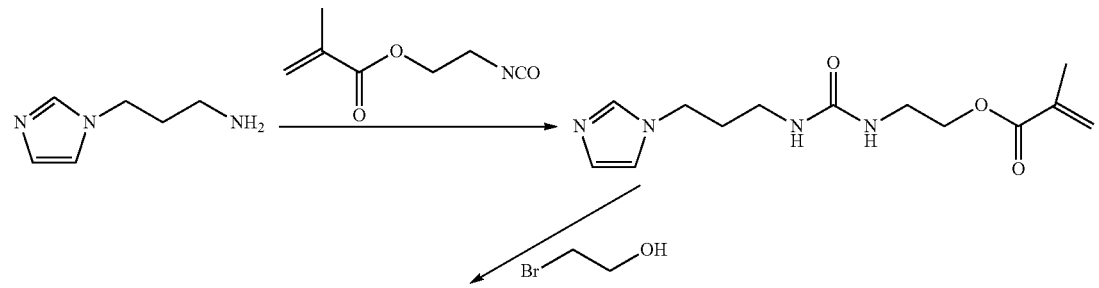

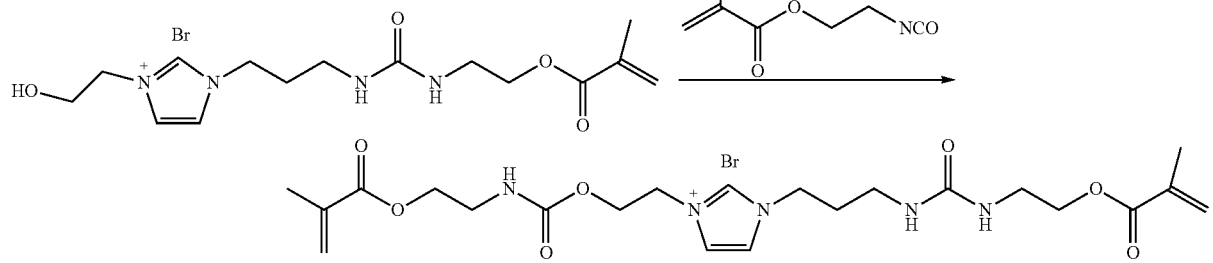

In addition to the (e.g. multifunctional) polymerizable ionic liquids described herein, the curable component of the composition can include a wide variety of other ethylenically unsaturated compounds (with or without acid functionality), epoxy-functional (meth)acrylate resins, vinyl ethers, and the like.

The (e.g., photopolymerizable) compositions may include compounds having free radically reactive functional groups that may include monomers, oligomers, and polymers having one or more ethylenically unsaturated group. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates).

Some illustrative examples of other polymerizable monomers, oligomers, or polymers useful herein include, for example, poly(meth)acryl monomers and mono(meth)acryl monomers such as (a) mono(meth)acryl containing compounds such as phenoxyethyl acrylate, ethoxylated phenoxyethyl acrylate, 2-ethoxyethoxyethyl acrylate, ethoxylated tetrahydrofurfural acrylate, and caprolactone acrylate, (b) di(meth)acryl containing compounds such as 1,3-butylene glycol diacrylate, 1,4-butanediol diacrylate, 1,6-hexanediol diacrylate, 1,6-hexanediol monoacrylate monomethacrylate, ethylene glycol diacrylate, alkoxylated aliphatic diacrylate, alkoxylated cyclohexane dimethanol diacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate; (c) tri(meth)acryl containing compounds such as glycerol triacrylate, trimethylolpropane triacrylate, pentaerythritol triacrylate, ethoxylated triacrylates (e.g., ethoxylated (3) trimethylolpropane triacrylate, ethoxylated (6) trimethylolpropane triacrylate, ethoxylated (9) trimethylolpropane triacrylate, ethoxylated (20) trimethylolpropane triacrylate, propoxylated triacrylates (e.g., propoxylated (3) glyceryl triacrylate, propoxylated (5.5) glyceryl triacrylate, propoxylated (3) trimethylolpropane triacrylate, propoxylated (6) trimethylolpropane triacrylate), trimethylolpropane triacrylate, tris(2-hydroxyethyl)isocyanurate triacrylate; (d) higher functionality (meth)acryl containing compounds such as pentaerythritol tetraacrylate, ditrimethylolpropane tetraacrylate, dipentaerythritol pentaacrylate, ethoxylated (4) pentaerythritol tetraacrylate, caprolactone modified dipentaerythritol hexaacrylate; (e) oligomeric (meth)acryl compounds such as, for example, urethane acrylates, polyester acrylates, epoxy acrylates; polyacrylamide analogues of the foregoing; and combinations thereof. Such compounds are widely available from vendors such as, for example, Sartomer Company of Exton, Pa.; UCB Chemicals Corporation of Smyrna, Ga.; Cytec Corporation, Cognis, and Aldrich Chemical Company of Milwaukee, Wis. Additional useful (meth)acrylate materials include hydantoin moiety-containing poly(meth)acrylates, for example, as described in U.S. Pat. No. 4,262,072 (Wendling et al.).

Other compounds that contain at least one ethylenically unsaturated bond include methyl(meth)acrylate, ethyl(meth)acrylate, isopropyl(meth)acrylate, n-hexyl (meth)acrylate, stearyl(meth)acrylate, allyl(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable (e.g. dental) composition may also contain hydroxyl groups and ethylenically unsaturated groups in a single molecule. Examples of such materials include hydroxyalkyl(meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis.

In certain embodiments curable components can include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate).

An initiator is typically added to the multifunctional polymerizable ionic liquid or to the mixture of polymerizable ingredients comprising at least one multifunctional polymerizable ionic liquid, as described herein. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the multifunctional polymerizable ionic liquid or composition comprising such is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate. Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition.

In some preferred embodiments, the curable composition may be irradiated with ultraviolet (UV) rays. For this embodiment, suitable photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably an ultraviolet or visible light source. It is convenient to employ light sources that emit actinic radiation light between 20 nm and 800 nm such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The multifunctional polymerizable ionic liquid or compositions comprising such may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

The compositions can also be cured with a thermally or heat activated free radical initiator. Typical thermal initiators include peroxides such as benzoyl peroxide and azo compounds such as azobisisobutyronitrile.

In some embodiments, such as when the composition comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such compositions comprising appreciable amounts of filler, the one or more multifunctional polymerizable ionic liquids are typically present in an amount totaling at least 5 wt-%, 6 wt-%, 7 wt-%, 8 wt-%, 9 wt-%, or 10 wt-%, based on the total weight of the composition. The concentration of multifunctional polymerizable ionic liquids is generally no greater than about 60 wt-%. In some embodiments the total amount of multifunctional polymerizable ionic liquids is at most 40 wt-%, preferably at most 30 wt-%, and more preferably at most 25 wt-%.

Compositions suitable for use as adhesives can also include filler in amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials, as known in the art.

The filler can be an inorganic material. It can also be a crosslinked organic material that is insoluble in the polymerizable resin, and is optionally filled with inorganic filler. The filler can be radiopaque, radiolucent, or nonradiopaque. Fillers can be ceramic in nature.

Inorganic filler particles include quartz (i.e., silica), submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911 (Kangas et al.), and U.S. Pat. No. 7,649,029 (Kolb et al.).

Examples of suitable organic filler particles include filled or unfilled pulverized polycarbonates, polyepoxides, poly(meth)acrylates and the like. Commonly employed filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in the resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_mSi(OR)_n$ or $CH_2=C(CH_3)_mC=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art. The curable composition may comprises various other ethylenically unsaturated monomer(s), oligomer(s), and polymer(s) and additive as known in the art, such as described in U.S. Provisional Application Ser. No. 61/289,098 titled "CURABLE DENTAL COMPOSITIONS AND ARTICLES COMPRISING POLYMERIZABLE IONIC LIQUIDS"; incorporated herein by reference.

The present invention will be further illustrated with reference to various dental compositions including dental adhesives as illustrative adhesives; dental sealants as illustrative coatings; and dental composites as illustrative articles having high mechanical strength. Articles, such as dental composites, can be made from the curable composition described herein by casting the curable composition in contact with a mold and curing the composition. Articles, such as dental composites, can alternatively be made by first curing the composition and then mechanically milling the composition into the desired article.

The curable blends of polymerizable ionic liquid in combination with convention (e.g. (meth)acrylate) ethylenically unsaturated monomers can be used for a variety of other uses, particularly (e.g. photo) curable coatings. A coated article can be prepared by applying the composition described herein to a substrate and curing the composition.

The curable blends can be applied to a variety of substrates. Suitable substrate materials include inorganic substrates such as glass or ceramics, natural and synthetic organic substrates such as paper, wood, as well as thermosetting or thermoplastic polymers such as polycarbonate, poly(meth)acrylate (e.g., polymethyl methacrylate or "PMMA"), polyolefins (e.g., polypropylene or "PP"), polyurethane, polyesters (e.g., polyethylene terephthalate or "PET"), polyamides, polyimides, phenolic resins, cellulose diacetate, cellulose triacetate, polystyrene, styrene-acrylonitrile copolymers, epoxies, and the like. The substrate thickness typically also will depend on the intended use. For most applications, substrate thicknesses of less than about 0.5 mm are preferred, and more preferably about 0.02 to about 0.2 mm. The substrate can be treated to improve adhesion between the substrate and curable coating compositions, e.g., chemical treatment, corona treatment such as air or nitrogen corona, plasma, flame, or actinic radiation. If desired, an optional tie layer or (e.g. polymerizable ionic liquid based) primer can be applied to the substrate to increase the interlayer adhesion.

The curable coating composition can be applied using a variety of conventional coating methods. Suitable coating methods include, for example, spin coating, knife coating, die coating, wire coating, flood coating, padding, spraying, roll coating, dipping, brushing, foam application, and the like. The coating is dried, typically using a forced air oven. The dried coating is at least partially and typically completely cured using an energy source.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

| Abbreviation | Chemical Description (Supplier, Location) |
|---|---|
| Polymerizable Monomer | |
| BisGMA | 2,2-bis[4-(2-hydroxy-3-methacryloyloxypropoxy)phenyl]propane |
| Bis EMA6 | ethoxylated bisphenol A methacrylate as further described in U.S. Pat. No. 6,030,606 available from Sartomer as "CD541" |
| TEGDMA | triethyleneglycol dimethacrylate |
| HEMA | 2-Hydroxyethyl methacrylate (Sigma-Aldrich, St. Louis, MO) |
| UDMA | Diurethane dimethacrylate (CAS No. 41137-60-4), commercially available as Rohamere 6661-0 (Rohm Tech, Inc., Malden, MA) |
| Inorganic Fillers | |
| S/T $TiO_2$ filler | Silane treated $TiO_2$ filler: The pH of an acetic acid water solution was adjusted to slightly less than 2.0 by adding 1.47 parts of acetic acid into 1.47 parts of DI water at room temperature. This solution was slowly added to 4.37 parts of methacryloxypropyltrimethoxy silane (available from GE Silicones under the trade designation "Silquest A-174") and 4.37 parts of methanol solution with stirring, stirring the solution for one hour. To this solution was added 96 parts of Ti Pure R-960 Titanium Dioxide from Dupont and 1.71 parts of Aerosil R-972 from Degussa, and mixed vigorously for about 10 minutes. The mixture was dried at 115° C. for 4 hours, crushed, and screened through a 74 micron nylon screen. |
| R812S Filler | Hydrophobic fumed silica available from Degussa Evonik Industries, Parsippany, NJ, under the trade designation "Aerosil Fumed Silica R812S". |
| Zr/Si Filler | One hundred parts zirconia silica filler of average particle size 0.6-0.9 micrometers was mixed with deionized water at a solution temperature of between 20-30° C., and the pH is adjusted to 3-3.3 with trifluoroacetic acid (0.278 parts). The A-174 silane was added to the slurry in an amount 7 parts, and the blend was mixed over 2 hours. At the end of 2 hours, the pH is neutralized with calcium hydroxide. The filler is dried, crushed and screened through a 74 or 100 micron screen. |
| Zr/Si Nano-Cluster Filler | Refers to silane-treated zirconia/silica nanocluster filler prepared essentially as described in U.S. Pat. No. 6,730,156 (Preparatory Example A (line 51-64) and Example B (column 25 line 65 through column 26 line 40). |
| 20 nm Si Nanomer Filler | Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2. |
| Components of Photointiator Package | |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; |
| EDMAB | ethyl 4-(N,N-dimethylamino)benzoate (Sigma-Aldrich) |

Synthesis of Polymerizable Ionic Liquids
Preparation of "PIL A"—Prep 1

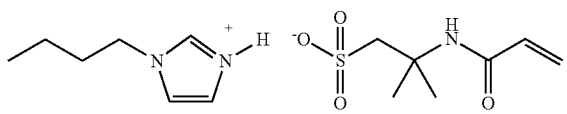

Butyl imidazole (4.82 g, 0.04 mol), BHT (0.015 g), and methanol (50 mL) were mixed with in a flask equipped with magnetic stirring. 2-acrylamido-2-methyl-1-propanesulfonic acid (8.05 g, 0.04 mol) and methanol (50 mL) were added at room temperature. The acid dissolved completely in 30 minutes. The reaction was stirred at room temperature overnight. The solvent was then removed under vacuum to give a viscous liquid.
Preparation of "PIL A-1"—Prep 2

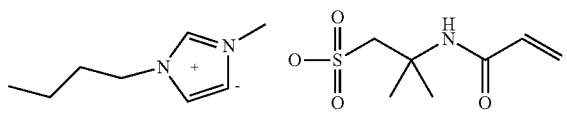

1-butyl-3-methylimidazolium hydrogen carbonate (Aldrich, 50% solution in methanol:water (2:3), 16 g, 0.04 mol), BHT (0.010 g), and methanol (20 mL) were mixed in a flask equipped with magnetic stirring. 2-acrylamido-2-methyl-1-propanesulfonic acid (8.28 g, 0.04 mol) and methanol (60 mL) were added while cooling the flash with a room temperature water bath. Carbon dioxide was generated and the mixture became clear. The reaction was stirred at room temperature for 4 hours. The solvent methanol and water was removed under vacuum to give a viscous liquid.
Preparation of PIL B

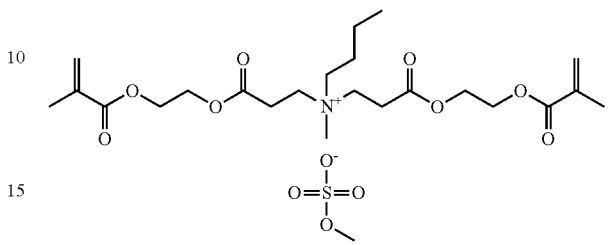

A mixture of n-butylamine (0.993 g, 14 mmol, Aldrich) and methacryloxyethyl acrylate (5.00 g, 27 mmol, prepared according to Klee, J. E., et. al., *Macromol. Chem. Phys.*, 200, 1999, 517) was stirred at room temperature for 24 hours. The intermediate product was a colorless liquid.

Dimethyl sulfate (0.57 g, 4.5 mmol) was added to the intermediate product from above (2.00 g, 4.5 mmol) dropwise over 10 minutes. The mixture was stirred for 17 hours to give the final PIL product as a thick liquid.
Preparation of PIL-C ("POS-2")

Polymerizable Onium Salt 2 (POS-2): represented by the following formula:

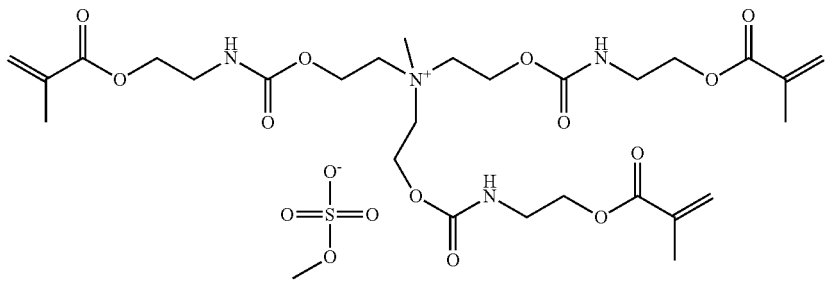

To a solution of tris-(2-hydroxyethyl)methylammonium methylsulfate (11.58 g, 0.04 mol, available from BASF), isocyanatoethyl methacrylate (19.58 g, 0.12 mol), and 2,6-di-tert-butyl-4-methylphenol (BHT, 0.020 g, available from Aldrich) in methylene chloride (50 mL) in a flask fitted with a drying tube and a magnetic stirrer was added a drop of dibutyltin dilaurate. The solution was cooled in an ice bath and stirred for 3 hours, then allowed to warm to room temperature and stirring was continued for another 36 hours. Progress of the reaction was monitored by infrared spectroscopy, observing the disappearance of the isocyanate absorption. When reaction was complete the solvent was removed at reduced pressure yielding a very viscous liquid.
Preparation of PIL D

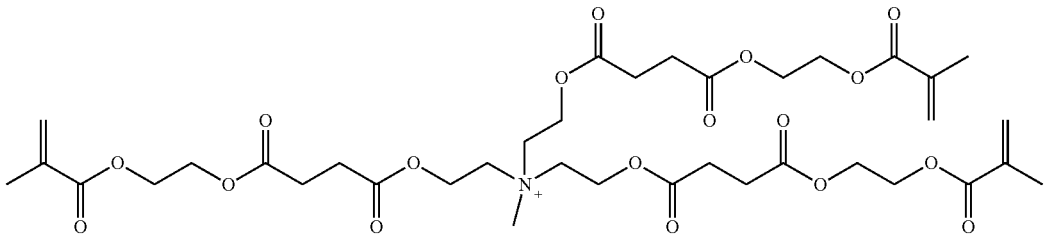

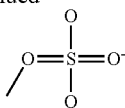

To a stirred, ice cooled solution of tris-(2-hydroxyethyl)methylammonium methylsulfate (17.38 g, 0.06 mol), mono-2-(methacryloyloxy)ethyl succinate (41.42 g, 0.18 mol, available from Aldrich), and 4-dimethylaminopyridine (1.098 g, 0.009 mol, available from Aldrich) in ethyl acetate (150 mL) was added dropwise over a 2 hour period a solution of 1,3-dicyclohexylcarbodiimide (DCC, 37.1 g, 0.18 mol, available from Aldrich) in ethyl acetate (150 mL). After the DCC solution was added, the temperature of the reaction mixture was allowed to rise gradually to room temperature, and then the reaction was stirred for 14 hours. Then 0.5 g of deionized water and 2.0 g of silica gel were added into the flask and the reaction mixture stirred for 1 hour. The mixture was then filtered and solvent removed from the filtrate at reduced pressure to yield a very viscous liquid product having a slight yellow color.

Preparation of PIL E

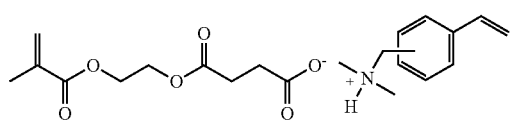

Into a vial was placed 1.000 g (6.2 mmol) of N,N-dimethyl vinyl benzylamine (mixture of isomers, Aldrich) and 1.428 g (6.2 mmol) mono-(methacryloxy)ethyl succinate (Aldrich). After mixing for 5 minutes the liquid product was obtained.

Preparation of PIL F

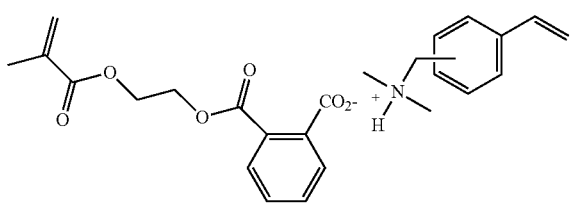

Into a vial was placed 1.000 g (6.2 mmol) of N,N-dimethyl vinyl benzylamine (mixture of isomers, Aldrich) and 1.726 g (6.2 mmol) mono-(methacryloxy)ethyl phthalate (Aldrich). After mixing for 5 minutes a liquid product was obtained.

Preparation of PIL G

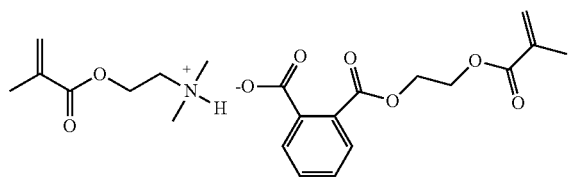

A mixture of dimethylaminoethyl methacrylate (56.62 g, 0.36 mol), Prostab 5198 (17 mg), and mono-2-(methacryloxy)ethyl phthalate (Aldrich, 100.00 g, 0.36 mol) was placed in a jar. The jar was capped and rolled at room temperature for 17 hours. A colorless oil was obtained.

Preparation of PIL H

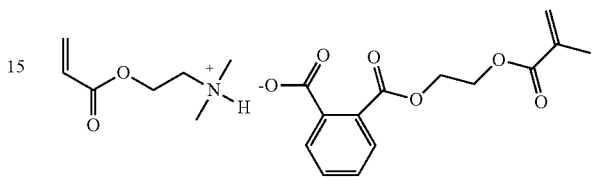

A mixture of dimethylaminoethyl acrylate (51.47 g, 0.36 mol), Prostab 5198 (17 mg), and mono-2-(methacryloxy)ethyl phthalate (100.00 g, 0.36 mol) was placed in a jar. The jar was capped and rolled at room temperature for 17 hours. A colorless oil was obtained.

Preparation of PIL I

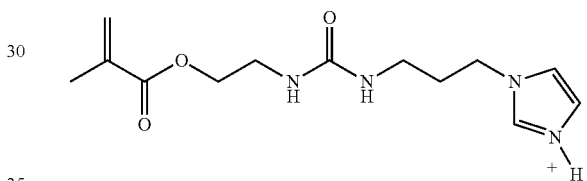

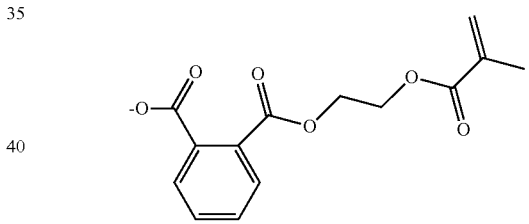

N-(3-aminopropyl)imidazole (Alfa Aesar, 2.55 g, 0.02 mol) and tetrahydrofuran (Alfa Aesar, 30 mL) were placed an a flask with magnetic stirring. 2-Isocyanatoethyl methacrylate (Showa Denko, Japan, 3.26 g, 0.02 mol) was added dropwise over 30 minutes while cooling the flask in an ice water bath. After three hours, mono-2-(methacryloxy)ethyl phthalate (5.67 g, 0.02 mol) and tetrahydrofuran (10 mL) were added and the mixture was stirred for three hours at room temperature. The solvent was removed under vacuum to give thick liquid product.

Determination of Air to Nitrogen Curing Exotherm Ratio:

The photo polymerization behavior of monomers under N2 and air was examined using differential scanning photocalorimetry (photo DSC). The photo DSC was a TA instrument (New Castle, Del.) with DSC module 2920. The light source was a mercury/argon lamp with an Oriel PN 59480 425 nm long pass light filter. The light intensity was 3 mW/cm$^2$, measured using an International Light light meter Model IL 1400 equipped with a Model XRL, 340A detector. The photo curable samples contained 0.5% camphorquinone (Sigma-Aldrich), 1.0% ethyl 4-(N,N-dimethylamino)benzoate (Sigma-Aldrich) and 1.0% diphenyl iodium hexafluorophosphate as the photoinitiator package. A 10 mg cured sample was used as a reference.

About 10 mg of the sample was weighed accurately for the testing with a Hermetic Pan (aluminum sample pan) as the sample holder. The samples were equilibrated at 37° C. for 5 minutes, and then the light aperture was opened to irradiate the sample. During irradiation the sample temperature was held at 37° C. The total irradiation time was 30 minutes. After 30 minutes, the aperture was closed and the sample maintained at 37° C. for another 5 minutes. The samples were tested under nitrogen and air atmosphere respectively.

The data was collected as heat output per unit weight (mW/g). The data was analyzed using TA Thermal Solutions Universal Analysis software.

Monomers were run once under nitrogen, then an identical sample was run under air. The DSC recorded the heat generation from the curing sample during exposure, and the area under the curve was integrated to give total Joules/gram of the monomer. The heat generated when the sample was cured in air was divided by the heat generated when the sample was cured in nitrogen to give the curing ratio. A higher ratio represents less oxygen inhibition.

Testing Results for Photocuring a Monofunctional PIL and 2-Hydroxyethyl Methacrylate (HEMA, Available from Aldrich) by Photo DSC

|  | Curing ratio (air/N2) |
| --- | --- |
| 90 wt % PIL-A/10 wt % HEMA | 0.90 |
| 80 wt % PIL-A/20 wt % HEMA | 0.89 |
| 70 wt % PIL-A/30 wt % HEMA | 0.87 |
| 60 wt % PIL-A/40 wt % HEMA | 0.88 |
| 50 wt % PIL-A/50 wt % HEMA | 0.84 |
| 40 wt % PIL-A/60 wt % HEMA | 0.58 |
| 30 wt % PIL-A/70 wt % HEMA | 0.46 |
| 20 wt % PIL-A/80 wt % HEMA | 0.35 |
| 10 wt % PIL-A/90 wt % HEMA | 0.25 |

Testing Results for Photocuring a Multifunctional PIL and Triethylene Glycol Dimethacrylate (TEGDMA, Available from Aldrich) by Photo DSC

|  | Curing ratio (air/N2) |
| --- | --- |
| 100 wt % PIL-C | 0.97 |
| 90 wt % PIL-C/10 wt % TEGDMA | 0.95 |
| 80 wt % PIL-C/20 wt % TEGDMA | 0.93 |
| 70 wt % PIL-C/30 wt % TEGDMA | 0.94 |
| 60 wt % PIL-C/40 wt % TEGDMA | 0.90 |
| 50 wt % PIL-C/50 wt % TEGDMA | 0.84 |
| 40 wt % PIL-C/60 wt % TEGDMA | 0.79 |
| 30 wt % PIL-C/70 wt % TEGDMA | 0.78 |
| 20 wt % PIL-C/80 wt % TEGDMA | 0.60 |
| 10 wt % PIL-C/90 wt % TEGDMA | 0.40 |
| 100 wt % TEGDMA | 0.36 |

Testing Results for Photocuring a Multifunctional PIL Comprising a Polymerizable Cation and Polymerizable Anion by Photo DSC

|  | Curing ratio (air/N2) |
| --- | --- |
| 100 wt % PIL-E | 0.79 |
| 100 wt % PIL-F | 0.94 |
| 100 wt % PIL-G | 0.97 |
| 100 wt % PIL-H | 1.00 |
| 100 wt % PIL-I | 0.98 |

Test Method for Evaluating Bond Strength of Dental Adhesive and Dental Sealant to Dental Hard Tissues Potted bovine teeth were ground using 120 grit sand paper to expose enamel or dentin, then teeth were further polished using 320 grit sand paper to smooth the surface. The bovine tooth surface was dried by applying a stream of compressed air for 3 seconds, then a drop of primer was applied, scrubbed for 20 seconds, dried by a stream of compressed air for 20 seconds, followed by application of a thin layer of adhesive (the adhesive composition is described below) with scrubbing for 20 seconds. The primer and adhesive combination was then cured for 20 seconds with a dental blue curing (3M ESPE Elipar Freelight 2) for 20 seconds. Previously prepared molds made from a 2.5-mm thick "Teflon" sheet with a 4.7 mm diameter hole through the sheet were clamped to each prepared tooth so that the central axis of the hole in the mold was normal to the tooth surface. The hole in each mold was filled with a visible light-curable dental restorative (available from 3M ESPE as "Filtek™ Z250 Restorative" A2 shade) and cured for 20 seconds irradiation with the dental curing light. The teeth and molds were allowed to stand for about 5 minutes at room temperature, then stored in distilled water at 37° C. for 24 hours unless otherwise noted. The molds were then carefully removed from the teeth, leaving a molded button of restorative attached to each tooth.

The adhesive strength was evaluated utilizing the wire loop method by mounting the acrylic disk in a holder clamped in the jaws of an "Instron 1123" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed using a crosshead speed of 2 mm/min. Five adhesion samples were prepared for each set of primer and adhesive.

Control Primer A

| Component | Wt-% |
| --- | --- |
| Maleic Acid | 10 |
| HEMA | 45 |
| Water | 45 |
| Total | 100.0 |

Dental Primer B

| Component | Wt-% |
| --- | --- |
| Maleic Acid | 10 |
| PIL A - Prep 1 | 45 |
| Water | 45 |
| Total | 100.0 |

Example 1

Dental Adhesive

| Component | Wt-% Solids | Weight, g |
| --- | --- | --- |
| PIL-C | 68.3 | 1.4 |
| HEMA | 0.0 | 0 |
| TEGDMA | 29.3 | 0.6 |
| CPQ | 0.5 | 0.01 |

| Component | Wt-% Solids | Weight, g |
|---|---|---|
| EDMAB | 1.0 | 0.02 |
| DPIHFP | 1.0 | 0.02 |
| total | 100 | 2.05 |

The test results of utilizing a conventional dental primer (Control Primer A), without a polymerizable ionic liquid in combination with a dental adhesive (Example 1), comprising a polymerizable ionic liquid were as follows:

| | Enamel Bond Strength (MPa) | Std. Dev. | Dentin Bond Strength (MPa) | Std. Dev. |
|---|---|---|---|---|
| Control Dental Adhesive | 11.6 | 4.3 | 10.9 | 2.3 |
| Example 1 | 14.3 | 3.9 | 13.9 | 3.1 |

Example 2

Dental Adhesive

| Component | Wt-% Solids | Weight, g |
|---|---|---|
| PIL C | 9.8 | 0.2 |
| HEMA | 0.00 | 0 |
| TEGDMA | 87.8 | 1.8 |
| CPQ | 0.5 | 0.01 |
| EDMAB | 1.0 | 0.02 |
| DPIHFP | 1.0 | 0.02 |
| Total | 100 | 2.05 |

Using Dental Primer B as the primer, the dental adhesive of Example 2, (i.e. containing PIL C) was evaluated in the same manner as previously described and compared to the Control Dental Adhesive.

| | Enamel Bond Strength (MPa) | Std. Dev. | Dentin Bond Strength (MPa) | Std. Dev. |
|---|---|---|---|---|
| Example 2 | 18.6 | 3 | 21.2 | 1.2 |
| Control Dental Adhesive | 15.8 | 5.8 | 13.4 | 2.1 |

The results show that the highest bond strength was achieved with a polymerizable ionic liquid based primer in combination with a polymerizable ionic liquid based adhesive.

Control Dental Sealant

| Component | Wt-% Solids | Weight, g |
|---|---|---|
| BisGMA | 46.35 | 2.00 |
| TEGDMA | 46.35 | 2.00 |
| CPQ | 0.23 | 0.01 |
| EDMAB | 1.16 | 0.05 |
| DPIHFP | 0.58 | 0.025 |
| S/T TiO2 Filler | 0.70 | 0.03 |
| R812S Filler | 4.63 | 0.20 |
| Total | 100 | 4.32 |

Example 3

Dental Sealant

| Component | Wt-% Solids | Weight, g |
|---|---|---|
| PIL C | 74.16 | 3.2 |
| TEGDMA | 18.54 | 0.8 |
| CPQ | 0.23 | 0.01 |
| EDMAB | 1.16 | 0.05 |
| DPIHFP | 0.58 | 0.025 |
| S/T TiO2 Filler | 0.70 | 0.03 |
| R812S Filler | 4.63 | 0.20 |
| Total | 100 | 4.32 |

Example 4

Dental Sealant

| Component | Wt-% Solids | Weight, g |
|---|---|---|
| PIL D | 74.16 | 3.2 |
| TEGDMA | 18.54 | 0.8 |
| CPQ | 0.23 | 0.01 |
| EDMAB | 1.16 | 0.05 |
| DPIHFP | 0.58 | 0.025 |
| S/T TiO2 Filler | 0.70 | 0.03 |
| R812S Filler | 4.63 | 0.20 |
| Total | 100 | 4.32 |

| | Enamel Bond Strength (MPa) | Std. Dev. | Curing ratio (air/nitrogen) |
|---|---|---|---|
| Example 3 | 16.0 | 2.9 | 0.96 |
| Example 4 | 15.2 | 1.1 | 0.88 |
| Control Sealant | 13.2 | 2.8 | 0.71 |

Test Methods for Evaluating Composite:

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample.

Barcol Hardness Test Method

Barcol Hardness of a test sample was determined according to the following procedure. An uncured composite sample was cured in 2.5-mm thick TEFLON mold sandwiched between a sheet of polyester (PET) film and a glass slide for 30 seconds and cured with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure. Results were reported as the average of three measurements.

Diametral Tensile Strength (DTS) Test Method DTS of a test sample was prepared according to the following procedure.

An uncured sample was injected into a 4-mm (inside diameter) glass tube that was capped with silicone rubber plugs; and then the tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). Cured samples were allowed to stand for 1 hour at about 37° C./90%+Relative Humidity and then were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Five cylinders of cured samples were prepared and measured with the results reported in MPa as the average of the five measurements.

For each of the following experiments, the Control Dental Composite was a commercially available dental material available from 3M ESPE under the trade designation "Filtek™ Z250 Restorative".

Example 5

Dental Composite

|  | Wt-% Total Composition | Wt-% of Resin | Weight - grams |
|---|---|---|---|
| Part A—Resin Component |  |  |  |
| PIL C | 12.636 | 63.18 | 3.1590 |
| UDMA | 4 | 20 | 1.0000 |
| TEGDMA | 3 | 15 | 0.7500 |
| CPQ | 0.034 | 0.17 | 0.0085 |
| EDMAB | 0.2 | 1 | 0.0500 |
| DPIHFP | 0.1 | 0.5 | 0.0250 |
| BHT | 0.03 | 0.15 | 0.0075 |
| Part B Zr/Si filler | 80 | NA | 20 |
| Total | 100 | 100 | 25 |

The methacrylates monomers, polymerizable ionic liquids C, photoinitiator, and BHT were mixed in a medium cup. Zr/Si filler (13 g) was added and mixed for 3 minutes at a mixing speed of 3500 rpm. The mixture was allowed to cool down and an additional 5.0 g of Zr/Si filler was added and mixed at 3500 rpm for 1.5 minutes. The mixture was allowed to cool down again and then 1 g of Zr/Si filler was added and mixed at 3500 rpm for 1.5 minutes. After cooling, 1.0 g of Zr/Si filler was added and speed mixed at 3500 rpm for 1.5 minutes. After cooling, it was speed mixed further for 1.5 minutes to give the final paste.

|  | DTS (MPa) | Std. Dev. | Shrinkage (%) | Std. Dev. | Hardness | Std. Dev. | Curing ratio (air/nitrogen) |
|---|---|---|---|---|---|---|---|
| Example 5 | 90.2 | 8.8 | 2.3 | 0.03 | 82.7 | 0.6 | 0.99 |
| Control Dental Composite | 90.9 | 10.4 | 2.1 | 0.05 | 83.5 | 1.4 | 0.85 |

Example 6

Dental Composite

|  | Wt-% Total Composition | Wt-% Resin | Weight grams |
|---|---|---|---|
| Part A—Resin Component |  |  |  |
| PIL D | 13.08 | 68.18 | 3.4 |
| BisEMA6 | 5.77 | 30.00 | 1.5 |
| CPQ | 0.03 | 0.17 | 0.009 |
| EDMAB | 0.10 | 1.00 | 0.025 |
| DPIHFP | 0.19 | 0.50 | 0.05 |
| BHT | 0.03 | 0.15 | 0.008 |
| Part B—Zr/Si filler | 80.77 | NA | 21 |
| Total | 100 | 100 | 26 |

Example 7

Dental Composite

|  | Wt-% Total Composition | Wt-% Resin | grams |
|---|---|---|---|
| Part A—Resin Component |  |  |  |
| PIL D | 20.45 | 98.18 | 4.909 |
| CPQ | 0.04 | 0.17 | 0.0085 |
| EDMAB | 0.10 | 0.50 | 0.025 |
| DPIHFP | 0.21 | 1.00 | 0.05 |
| BHT | 0.03 | 0.15 | 0.0075 |
| Part B—Zr/Si filler | 79.17 | NA | 19 |
| Total | 100 | 100 | 24 |

|  | DTS (MPa) | Std. Dev. | Shrinkage, vol % | Std. Dev. | Hardness | Std. Dev. |
|---|---|---|---|---|---|---|
| Example 6 | 92.3 | 5.5 | 1.84 | 0.03 | 86.2 | 1.3 |
| Example 7 | 85.6 | 5.2 | 1.84 | 0.02 | 87.6 | 1.1 |
| Control Dental Composite | 95.3 | 7.1 | 1.89 | 0.02 | 85.5 | 1.4 |

Example 8

Dental Composite

|  | Wt-% Total Composition | Wt-% Resin | grams |
|---|---|---|---|
| Part A—Resin Component |  |  |  |
| PIL D | 9.06 | 48.20 | 2.41 |
| UDMA | 8.46 | 45.00 | 2.25 |
| TEGDMA | 0.94 | 5.00 | 0.25 |
| CPQ | 0.03 | 0.17 | 0.0085 |
| EDMAB | 0.09 | 0.50 | 0.025 |
| DPIHFP | 0.19 | 1.00 | 0.05 |
| BHT | 0.03 | 0.15 | 0.0075 |

| | | | | | |
|---|---|---|---|---|---|
| Part B—Zr/Si filler | 81.20 | | NA | | 21.6 |
| Total | 100 | | 100 | | 26.6 |

| | DTS (MPa) | Std. Dev. | Shrinkage (%) | Std. Dev. | Hardness | Std. Dev. |
|---|---|---|---|---|---|---|
| Example 8 | 104 | 4.5 | 2.0 | 0.04 | 85.3 | 1.6 |
| Control Dental Composite | 88.6 | 6.3 | 1.9 | 0.02 | 86.5 | 1.0 |

Example 9

Dental Composite

| | Wt-% Total Composition | Wt-% Resin | grams |
|---|---|---|---|
| Part A—Resin Component | | | |
| PIL D | 11.47 | 48.18 | 2.409 |
| UDMA | 8.57 | 36.00 | 1.8 |
| TEGDMA | 3.33 | 14.00 | 0.7 |
| CPQ | 0.04 | 0.17 | 0.0085 |
| EDMAB | 0.12 | 0.50 | 0.025 |
| DPIHFP | 0.24 | 1.00 | 0.05 |
| BHT | 0.04 | 0.15 | 0.0075 |
| Part B—20 nm silica nanomer filler | 7.62 | NA | 1.6 |
| Part B—Zr/Si nano cluster filler | 68.57 | NA | 14.4 |
| Total | 100 | 100 | 21.0 |

Liquid components were mixed at 3500 rpm for 2.5 minutes, and formed a clear solution. 1.0 g 20 nm silica nanomer filler and 9.0 g Si/Zr nano-cluster filler were mixed first, then added into the resin, speed mixed at 2000 rpm for 1 minute, then speed mixed at 3500 rpm for 2 minutes. 20 nm Si nanomer filler (0.3 g) and Si/Zr nano-cluster filler (2.97 g) were added, then speed mixed at 3500 rpm for 2 minutes. 20 nm Si nanomer filler (0.3 g) and Si/Zr nano-cluster filler (2.70 g) were added then speed mixed at 3500 rpm for 2 minutes, to give the final paste.

Control is Filtek™ Supreme Universal Restorative Composite

| | DTS (MPa) | Std. Dev. | Shrinkage | Std. Dev. |
|---|---|---|---|---|
| Example 9 | 73.0 | 7.9 | 1.9 | 0.02 |
| Control Dental Composite | 81.1 | 3.3 | 1.9 | 0.02 |

UV Cure Clear Coating Examples:

The indicated polymerizable ionic liquid, other monomers (HEMA or TEDGMA, from Aldrich) and UV initiator (TPO-L, available from BASF, or Darocur 1173 from Ciba) were mixed in a speed mixing cup to form clear solution. A drop of coating material was dropped on glass slides with cotton tipped applicator and let the solution spread out with the applicator. Coated glass slides were passed through a Fusion F 300 UV curing line under air atmosphere. A UV H-bulb was used and UV intensity was measured at 9 fpm in air as following, total energy dentist (mJ/cm$^2$), UVA was 1004, UVB was 987, UVC was 153, UVV was 1232.

Using nitrile gloves, the cured coating was touched by hand to check the curing degree. The curing degree was rated as cure or no cure, and surface inhibition was rates as no coating liquid smear layer transfer or smear layer transfer to glove. Detailed formulation, curing speed and curing results is listed in the following table.

| PIL | Wt (g) | Other Monomer | Wt (g) | Photo initiator | Wt (mg) | 23 fpm | 9 fpm |
|---|---|---|---|---|---|---|---|
| Ex. 10 PIL-C | 0.805 | TEGDMA | 0.207 | Lucerin TPO-L | 29.2 | Cured - no transfer | Cured - no transfer |
| Ex. 11 PIL-C | 0.886 | TEGDMA | 0.200 | Darocur 1173 | 28.6 | Cured - no transfer | Cured - no transfer |
| Ex. 12 PIL-D | 0.772 | TEGDMA | 0.191 | Lucerin TPO-L | 31.0 | Cured - no transfer | Cured - no transfer |
| Ex. 13 PIL-D | 0.828 | TEGDMA | 0.194 | Darocur 1173 | 28.8 | Cured - no transfer | Cured - no transfer |
| Ex. 14 PIL-A | 0.893 | TEGDMA | 0.106 | Lucerin TPO-L | 29.1 | Cured - no transfer | Cured - no transfer |
| Ex. 15 PIL-A | 0.902 | TEGDMA | 0.106 | Darocur 1173 | 31.2 | Cured - no transfer | Cured - no transfer |
| Ex. 16 PIL-C | 0.803 | HEMA | 0.209 | Lucerin TPO-L | 30.4 | Cured - no transfer | Cured - no transfer |
| Ex. 17 PIL-C | 0.817 | HEMA | 0.198 | Darocur 1173 | 30.1 | Cured - no transfer | Cured - no transfer |
| Ex. 18 PIL-D | 0.849 | HEMA | 0.202 | Lucerin TPO-L | 28.8 | Cured - transfer | Cured - transfer |
| Ex. 19 PIL-D | 0.799 | HEMA | 0.204 | Darocur 1173 | 28.8 | Cured - no transfer | Cured - no transfer |
| Ex. 20 PIL-C | 0.735 | TEGDMA | 0.292 | Lucerin TPO-L | 30.0 | Cured - no transfer | Cured - no transfer |
| Ex. 21 PIL-C | 0.714 | TEGDMA | 0.299 | Darocur 1173 | 29.3 | Cured - no transfer | Cured - no transfer |
| Ex. 22 PIL-D | 0.716 | TEGDMA | 0.293 | Lucerin TPO-L | 30.0 | Cured - transfer | Cured - transfer |
| Comp A | 0 | TEGDMA | 1.00 | Lucerin TPO-L | 32 | NA | partially cured - transfer |

-continued

| PIL | Wt (g) | Other Monomer | Wt (g) | Photo initiator | Wt (mg) | 23 fpm | 9 fpm |
|---|---|---|---|---|---|---|---|
| Comp B | 0 | TEGDMA | 1.01 | Darocur 1173 | 26 | NA | partially cured - transfer |
| Comp C | 0 | HEMA | 1.01 | Lucerin TPO-L | 30 | NA | partially cured - transfer |
| Comp D | 0 | HEMA | 1.01 | Darocur 1173 | 30 | NA | partially cured - transfer |
| Comp E | 0 | BisGMA/TEGDMA (50/50) | 1.00 | Lucerin TPO-L | 32 | NA | partially cured - transfer |
| NA | 0 | BisGMA/TEGDMA (50/50) | 1.00 | Darocur 1173 | 30 | NA | partially cured - transfer |

The results show that the inclusion of a polymerizable ionic liquid can improve the curing in air. Examples 13, 18, 19, and 22 demonstrate that Darocur 1173 photoinitiator is preferred for blends of HEMA or TEGMA with PIL-D.

UV Cured White Colored Coating Examples:

The indicated polymerizable ionic liquid, TEGDMA, titanium dioxide ($TiO_2$) and UV initiator (Darocur 1173 from Ciba) were mixed in a speed mixing cup to form white color coating composition. A drop of coating material was applied on glass slides with cotton tipped applicator and let the solution spread out with the applicator. Coated glass slides were passed through a Fusion F 300 UV curing line under air atmosphere. A UV H-bulb was used and UV intensity was measured at 9 fpm in air as following, total energy dentist ($mJ/cm^2$), UVA was 1004, UVB was 987, UVC was 153, UVV was 1232.

A cotton-tipped applicator was used to touch the sample after curing to check the curing degree. The curing degree was rated as cure or no cure. Detailed formulation, curing speed and curing results were listed in the following table.

| | Composition | | | | Curing line speed and curing results | | |
|---|---|---|---|---|---|---|---|
| PIL | PIL Wt (g) | $TiO_2$ Wt (g) | TEGDMA Wt (g) | UV Initiator Wt (mg) | 3 fpm | 9 fpm | 23 fpm |
| PIL-D | 2.0 | 0.30 | NA | 0.0690 | Surface Cured - White | Surface Cured - White | Surface Cured - White |
| PIL-A | 2.0 | 0.30 | NA | 0.0730 | Surface Cured - Tan | Surface Cured - Tan | Surface Cured - White |
| PIL-D | 1.8 | 0.30 | 0.20 | 0.0650 | Surface Cured - Tan | Surface Cured - Tan | Surface Cured - White |
| PIL-A | 1.8 | 0.30 | 0.20 | 0.0680 | Surface Cured - Tan | Surface Cured - Tan | Surface Cured - White |
| PIL-D | 1.6 | 0.30 | 0.40 | 0.0700 | Surface Cured - Tan | Surface Cured - Tan | Surface Cured - White |
| PIL-A | 1.1 | 0.20 | 0.28 | 0.0457 | Surface Cured - White | Surface Cured - White | Surface Cured - White |
| Comp | 0.0 | 0.30 | 2.00 | 0.0680 | not cured | not cured | not cured |

What is claimed is:

1. A curable composition comprising a polymerizable organic composition comprising
    I) at least one multifunctional polymerizable ionic liquid comprising a cation and an anion, and at least two free-radically polymerizable groups selected from (meth)acrylamide, (meth)acrylate, or vinyl ether, the multifunctional polymerizable ionic liquid having an air to nitrogen curing exotherm ratio of at least 0.70; and ii) at least one other ethylenically unsaturated monomer, oligomer, or polymer.

2. The curable composition of claim 1 wherein the multifunctional polymerizable ionic liquid has an air to nitrogen curing exotherm ratio of at least 0.90.

3. The curable composition of claim 1 wherein the other ethylenically unsaturated monomer(s), oligomer(s), or polymer(s) has an air to nitrogen curing exotherm ratio of no greater than 0.50.

4. The curable composition of claim 1 wherein the curable composition comprises a photoinitiator.

5. The curable composition of claim 1 wherein the multifunctional polymerizable ionic liquid comprises an organic anion.

6. The curable composition of claim 1 wherein the multifunctional polymerizable ionic liquid comprises an aromatic carboxylate anion.

7. An article comprising the cured composition of previous claim 1.

8. An article comprising a substrate and the cured coating composition of claim 1 disposed on a surface of the substrate.

9. The curable composition of claim 1 wherein the multifunctional polymerizable ionic liquid has the formula

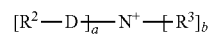

wherein
R³ is independently hydrogen or a C2-C8 alkyl group;
R² is a free-radically polymerizable group;
D is a divalent linking group comprising an aromatic moiety;
a is 1-4;
b is 0-3;
a+b=4; and
X⁻ is an organic cation comprising a free-radically polymerizable group;
and at least one of the free-radically polymerizable groups of R² or X⁻ is selected from (meth)acrylamide, (meth)acrylate, or vinyl ether.

10. The curable composition of claim 9 wherein the multifunctional polymerizable ionic liquid is

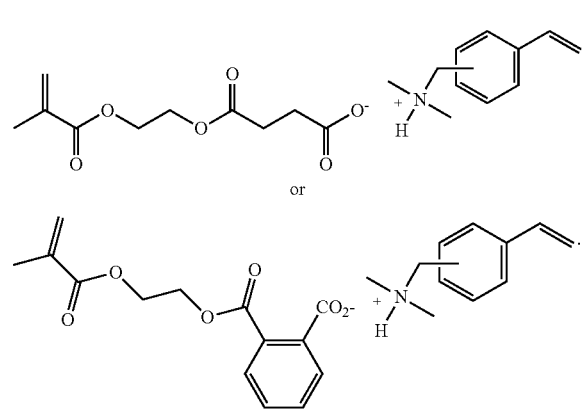

11. The curable composition of claim 1 wherein the multifunctional polymerizable ionic liquid has the formula

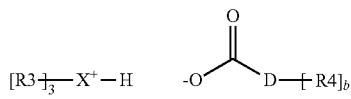

wherein
X is nitrogen or phosphorus;
R3 is independently alkyl or heteroalkyl, and at least one R3 further comprises a free-radically polymerizable group;
R4 is independently alkyl or heteroalkyl, and at least one R4 further comprises a free-radically polymerizable group;
at least one of the free-radically polymerizable groups of R3 or R4 is selected from (meth)acrylamide, (meth)acrylate, or vinyl ether;
D comprises an aromatic moiety and optionally comprises a linking group between the carboxylate end group and aromatic moiety and/or optionally comprises a linking group between the aromatic moiety and R4; and
b is 1-2.

12. The curable composition of claim 1 wherein the multifunctional polymerizable ionic liquid has the formula

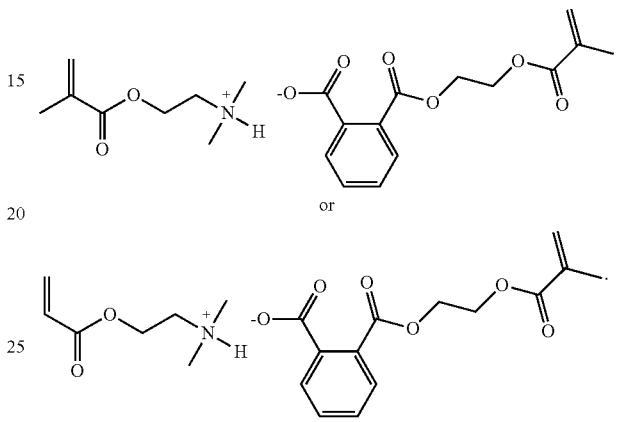

13. The curable composition of claim 1 wherein the polymerizable organic composition comprises at least 50 wt-% of multifunctional polymerizable ionic liquid.

14. The curable composition of claim 1 wherein curable composition comprises at least 40 wt-% of inorganic filler.

15. The curable composition of claim 1 wherein the filler comprises silica, zirconia, or mixtures thereof.

16. The curable composition of claim 1 wherein the filler has an average primary partilce size of less than 0.100 micrometers.

17. The curable composition of claim 1 wherein the ethylenically unsaturated monomer, oligomer, or polymer is selected from poly(meth)acryl monomers, mono(meth)acryl compounds, and oligomeric (meth)acryl compounds.

18. The curable composition of claim 1 wherein the curable composition can be completely cured in air.

19. A coated substrate comprising a substrate and the curable composition of claim 1 cured on a surface of the substrate.

* * * * *

UNITED STATES PATENT AND TRADEMARK OFFICE
CERTIFICATE OF CORRECTION

PATENT NO. : 8,816,029 B2
APPLICATION NO. : 13/380267
DATED : August 26, 2014
INVENTOR(S) : Yizhong Wang et al.

It is certified that error appears in the above-identified patent and that said Letters Patent is hereby corrected as shown below:

On the Title Page

Page 3, Column 1 (Other Publications)
Line 4, delete "Acryalte" and insert -- Acrylate --, therefor.

Line 33, delete "Polyer" and insert -- Polymer --, therefor.

Line 36, delete "Tatrahedron" and insert -- Tetrahedron --, therefor.

Line 66, delete "Termally" and insert -- Thermally --, therefor.

Page 3, Column 2 (Other Publications)
Line 24, delete "Electrom-Transfer" and insert -- Electron-Transfer --, therefor.

Line 66, delete "Evalutaion" and insert -- Evaluation --, therefor.

In the Specification

Column 2
Lines 36-37, delete "crosslinking" and insert -- crosslinking. --, therefor.

Column 3
Lines 6-7, delete "Unless otherwise noted, heteroalkyl groups may be mono- or polyvalent."
and insert the same on Col. 3 Line 5 as a continuation of the same paragraph.

Column 5
Line 11, delete "2-hydroxylethyl" and insert -- 2-hydroxyethyl --, therefor.

Line 13, delete "methacyloxypropoxy)" and insert -- methacryloxypropoxy) --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,816,029 B2

Column 19
Line 7, delete "1-methylheptyamine," and insert -- 1-methylheptylamine, --, therefor.

Column 21
Lines 61-62, delete "pentaerthyritol" and insert -- pentaerythritol --, therefor.

Column 22
Line 61, delete "3-ethacryloxypropoxy)" and insert -- 3-methacryloxypropoxy) --, therefor.

Column 23
Line 32, delete "tetrafluoroboarate." and insert -- tetrafluoroborate. --, therefor.

Column 28
Line 13, delete "dependant" and insert -- dependent --, therefor.

Column 30
Line 63 (approx.), delete "Photointiator" and insert -- Photoinitiator --, therefor.

Column 34
Lines 46-47 (approx.), delete "an a" and insert -- in a --, therefor.

In the Claims

Columns 43-44
Lines 62-66 (approx.) (Col. 43) 20-22 (Col. 44), in Claim 1, delete "at least one multifunctional polymerizable ionic liquid comprising a cation and an anion, and at least two free-radically polymerizable groups selected from (meth)acrylamide, (meth)acrylate, or vinyl ether, the multifunctional polymerizable ionic liquid having an air to nitrogen curing exotherm ratio of at least 0.70; and ii) at least one other ethylenically unsaturated monomer, oligomer, or polymer." and insert -- at least 30 wt-% of a multifunctional polymerizable ionic liquid comprising a substituted ammonium or phosphonium cation and an anion, wherein the cation and anion each comprise a free-radically polymerizable group and at least one free-radically polymerizable group is selected from (meth)acrylamide, (meth)acrylate, or vinyl ether; and the multifunctional polymerizable ionic liquid has an air to nitrogen curing exotherm ratio of at least 0.70; and ii) at least one other ethylenically unsaturated monomer, oligomer, or polymer. --, therefor.

Column 46
Line 38 (approx.), delete "partilce" and insert -- particle --, therefor.